United States Patent
Tanaka et al.

(10) Patent No.: US 7,491,833 B2
(45) Date of Patent: Feb. 17, 2009

(54) VALEROLACTONE COMPOUNDS AND PERFUME COMPOSITION

(75) Inventors: Sakuya Tanaka, Wakayama (JP); Kazuyuki Fukuda, Tokyo (JP); Takahiro Asada, Wakayama (JP)

(73) Assignee: Kao Corporation, Tokyo (JP)

( * ) Notice: Subject to any disclaimer, the term of this patent is extended or adjusted under 35 U.S.C. 154(b) by 621 days.

(21) Appl. No.: 10/529,290

(22) PCT Filed: Sep. 26, 2003

(86) PCT No.: PCT/JP03/12341
§ 371 (c)(1),
(2), (4) Date: Mar. 25, 2005

(87) PCT Pub. No.: WO2004/029033
PCT Pub. Date: Apr. 8, 2004

(65) Prior Publication Data
US 2006/0258559 A1   Nov. 16, 2006

(30) Foreign Application Priority Data
Sep. 27, 2002 (JP) .............. 2002-282675
Oct. 23, 2002 (JP) .............. 2002-308952
Sep. 16, 2003 (JP) .............. 2003-323125

(51) Int. Cl.
C07D 309/00 (2006.01)
A61Q 13/00 (2006.01)
(52) U.S. Cl. ............. 549/273; 512/11; 512/25
(58) Field of Classification Search ............ 549/455, 549/273; 512/25, 11
See application file for complete search history.

(56) References Cited

U.S. PATENT DOCUMENTS

| | | | |
|---|---|---|---|
| 3,380,457 A | 4/1968 | Schumacher et al. | |
| 3,825,572 A | 7/1974 | van Venrooy | |
| 4,288,350 A | 9/1981 | Nieuwland et al. | |
| 5,231,192 A | * 7/1993 | Rebrovic et al. ............ | 549/273 |

FOREIGN PATENT DOCUMENTS

| EP | 0 054 316 A1 | 6/1982 |
|---|---|---|
| EP | 0513627 | * 5/1992 |
| EP | 0 513 627 A1 | 11/1992 |
| EP | WO 94/07887 | * 4/1994 |
| EP | 0 952 226 A1 | 10/1999 |
| GB | 2 024 208 | 1/1980 |
| JP | 50-101563 | 8/1975 |
| JP | 53-84975 | 7/1978 |
| JP | 60-109537 | 6/1985 |
| JP | 62-5123 | 2/1987 |
| WO | WO 94/07887 | 4/1994 |

OTHER PUBLICATIONS

Tsunoi et al. Journal of the American Chemical Society (1998), 120(34), 8692-8701.*
Ihara et al. Journal of Organic Chemistry (1996), 61(2), 677-84.*
Tsunoi, Shinji et al. "New Strategies in Carbonylation Chemistry: The Synthesis of delta-Lactones from Saturated Alcohols and CO", J. Am. Chem. Soc., vol. 120, pp. 8692-8701 1998.
Ihara, Masataka et al. "Synthesis of Six-Membered Compounds by Environmentally Friendly Cyclization Using Indirect Electrolysis", J. Org. Chem., vol. 61, pp. 677-684 1996.

* cited by examiner

Primary Examiner—D. Margaret Seaman
Assistant Examiner—Nizal S Chandrakumar
(74) Attorney, Agent, or Firm—Oblon, Spivak, McClelland, Maier & Neustadt, P.C.

(57) ABSTRACT

A valerolactone compound represented by the formula (I):

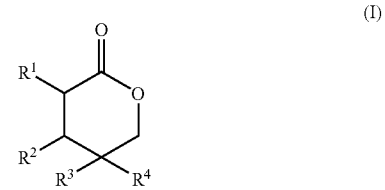

(I)

wherein each of $R^1$ and $R^2$ is independently a hydrogen atom, a methyl group or an ethyl group wherein when $R^1$ is a hydrogen atom, $R^2$ is not a hydrogen atom; and wherein when $R^2$ is a hydrogen atom, $R^1$ is not a hydrogen atom, $R^3$ is a hydrogen atom or a methyl group, and $R^4$ is a propyl group, a 1-propenyl group or a phenyl group; a valerolactone compound represented by the formula (II):

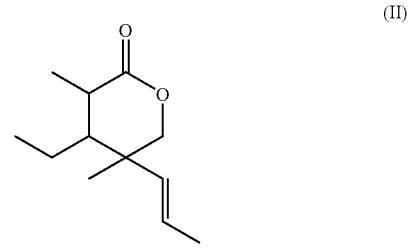

(II)

a process for preparing the same; and a perfume composition comprising the above-mentioned valerolactone compound.

21 Claims, 10 Drawing Sheets

CHEMICAL SHIFT (ppm)

CHEMICAL SHIFT (ppm)

CHEMICAL SHIFT (ppm)

CHEMICAL SHIFT (ppm)

VALEROLACTONE COMPOUNDS AND PERFUME COMPOSITION

CROSS REFERENCES TO RELATED APPLICATIONS

This application is a 371 of International patent application Ser. No. PCT/JPO3/12341, filed on Sept. 26, 2003, and claims priority to Japanese Patent Application No. 2002-282675, filed on Sept. 27, 2002, Japanese Patent Application No. 2002-308952, filed on Oct. 23, 2002, and Japanese Patent Application No. 2003-323125, filed on Sept. 16, 2003.

TECHNICAL FIELD

The present invention relates to a valerolactone compound and a process for preparing the same, and a perfume composition containing the valerolactone compound.

BACKGROUND ART

Sandalwood (Japanese name: Byakudan) which has been mainly produced in the eastern district of India has a noble characteristic odor. Therefore, sandalwood has been highly prized as a material for Buddhist statues and various craft carving materials in the Orient. An essential oil obtained from the core and root of the sandalwood by water steam distillation has been used as a perfume from old times. The characteristics of this sandalwood oil reside in that the sandalwood oil shows a soft and sweet woody odor and a balsamic odor, and has high sustainability odor. Therefore, the sandalwood oil has been widely used in oriental-type fragrance, perfume, cosmetics, soap, incense stick and the like (for example, see "Fundamental Knowledge of Perfumes and Flavor Preparation" authored and edited by Mototaka Nakajima, Sangyotosyo Kabushiki Kaisya, initial edition third printing (2000), p. 322-323).

However, with increased consciousness on environmental protection, and reinforcement of forest protection as flood control measures in recent years, there is a tendency that excessive felling of natural timber is suppressed. The amount of felling of sandalwood is restricted by the governments in the countries producing it, and deficient supply and cost increase of sandalwood oil has become a problem in the fragrance industry.

For this reason, as a substitute for sandalwood oil, sandalwood-type aroma chemicals such as 2-methyl-4-(2,2,3-trimethyl-3-cyclopenten-1-yl)-2-buten-1-ol, 2-ethyl-4-(2,2,3-trimethyl-3-cyclopenten-1-yl)-2-buten-1-ol, 3-methyl-5-(2,2,3-trimethyl-3-cyclopenten-1-yl)-pentan-2-ol, and isocamphylcyclohexanol have been used. However, these sandalwood-type aroma chemicals are deficient in the soft and characteristic sweet odor of natural sandalwood. Therefore, it is difficult to sufficiently reproduce the odor of natural sandalwood.

Generally, as a perfume supplementary to the sweet flavor of a perfume composition, there have been proposed esters, lactones, faranons, vanillins, and the like. Among them, lactones, for example, γ-pentyl-γ-butyrolactone (another name γ-nonalactone) and δ-pentyl-δ-valerolactone (another name δ-decalactone) have coconut-like and milk-like sweetness. Therefore, the lactones exhibit effects of producing food-like sweetness. It is said that γ-ethyl-γ-1-butenyl-δ-valerolactone (for example, see JP-A-Showa-53-84975) is costus-like lactone, and that saturated γ-ethyl-γ-butyl-δ-valerolactone (for example, trade name: COSTAULON manufactured by PFW) is costus-like and woody-like lactone.

In addition, as a lactone compound which can be used as a perfume, 4-cyclohexylpentanolide (for example, see JP-B-Showa-62-5123) and α-alkyl-β-alkyl-δ-alkyl-δ-valerolactone have been known (for example, see U.S. Pat. No. 3,380,457).

As explained above, since many of the above-mentioned lactones have no woody odor, even when the lactones are directly added to sandalwood-type aroma chemicals, the harmony of perfumes are insufficient, and moreover, food-like sweetness impairs the characteristics of the natural sandalwood. In addition, among the lactones, those having a woody odor show a strong costus-like odor, and are insufficient in sweetness. Therefore, even when they are added to sandalwood-type aroma chemicals, sweetness having a natural sandalwood-like sweetness cannot be supplemented. In other words, conventionally, the perfume compositions having a characteristic soft and sweet woody and balsamic odor of natural sandalwood have not yet been artificially obtained.

DISCLOSURE OF INVENTION

The present invention relates to a valerolactone compound represented by the formula (I):

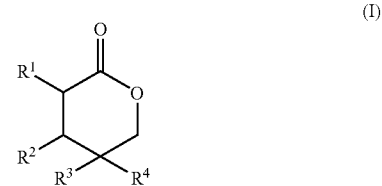

wherein each of $R^1$ and $R^2$ is independently a hydrogen atom, a methyl group or an ethyl group wherein when $R^1$ is a hydrogen atom, $R^2$ is not a hydrogen atom; and wherein when $R^2$ is a hydrogen atom, $R^1$ is not a hydrogen atom, $R^3$ is a hydrogen atom or a methyl group, and $R^4$ is a propyl group, a 1-propenyl group or a phenyl group.

SPECIFIC EXPLANATION OF INVENTION

More specifically, the present invention relates to a valerolactone compound which emits a lactone-like odor having coumarin-like sweetness reminding a woody and tonka beans-like odor, and is excellent in long-lasting effect, and a perfume composition containing the above-mentioned valerolactone compound, which exhibits characteristics of natural sandalwood.

The present inventors have found that a valerolactone compound represented by the formula (I) described below emits a characteristic odor having both a woody and a coumarin-like sweet odor, that the odor can bring out a sweet odor harmonized with a woody odor, and that characteristics of natural sandalwood which have been insufficient in sandalwood-type aroma chemicals can be easily exhibited when the valerolactone compound is particularly combined with a sandalwood-type aroma chemicals.

Also, a valerolactone compound represented by the formula (II) of the preset invention can be prepared by acting a base on propanal, and treating the resulting reaction solution with an acid. Alternatively, the valerolactone compound represented by the formula (II) of the present invention can be prepared by acting a base on 2-methyl-2-pentenal, and treating the resulting solution with an acid.

The present invention enables to provide a perfume composition having a sweet odor harmonized with a woody odor by including the valerolactone compound represented by the formula (I) in the composition. Moreover, the present invention enables to impart a sweet odor matching with a woody odor close to that of natural sandalwood to household products, personal care and cosmetic products, environmental hygiene products, beverages and foods by including the perfume composition in those products.

The valerolactone compound of the present invention is (1) a valerolactone compound represented by the formula (I):

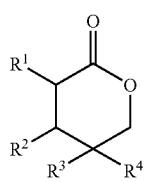
(I)

wherein each of $R^1$ and $R^2$ is independently a hydrogen atom, a methyl group or an ethyl group wherein when $R^1$ is a hydrogen atom, $R^2$ is not a hydrogen atom; and wherein when $R^2$ is a hydrogen atom, $R^1$ is not a hydrogen atom, $R^3$ is a hydrogen atom or a methyl group, and $R^4$ is a propyl group, a 1-propenyl group or a phenyl group.

(2) Also, the valerolactone compound of the present invention is a valerolactone compound represented by the formula (II):

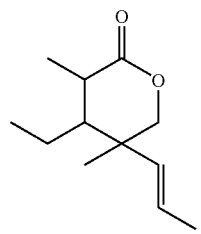
(II)

(3) The valerolactone compound of the present invention is a valerolactone compound represented by the formula (II) obtained by acting a base on propanal, and treating the resulting reaction solution with an acid.

(4) The process for preparing the valerolactone compound of the present invention is a process for preparing a valerolactone compound represented by the formula (II), which contains acting a base on propanal, and treating the resulting reaction solution with an acid.

(5) The process for preparing the valerolactone compound of the present invention is a process for preparing a valerolactone compound represented by the formula (II), which contains acting a base on 2-methyl-2-pentenal, and treating the resulting reaction solution with an acid.

(6) The perfume composition of the present invention is a perfume composition which contains a valerolactone compound represented by the formula (I).

(7) The perfume composition of the present invention is a perfume composition which contains a valerolactone compound represented by the formula (II).

(8) The perfume composition of the present invention is a perfume composition which contains a valerolactone compound described in the above item (3).

(9) The perfume composition of the present invention is also a perfume 20 composition which contains one or more compounds selected from the group consisting of the compounds represented by the following formulae (III) to (VII):

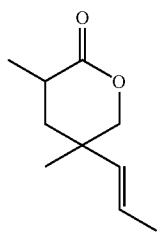
(III)

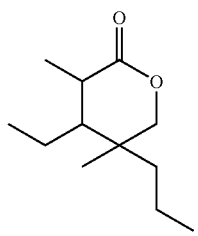
(IV)

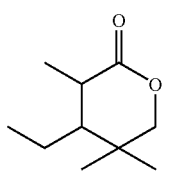
(V)

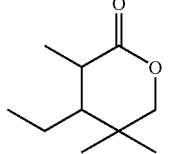
(VI)

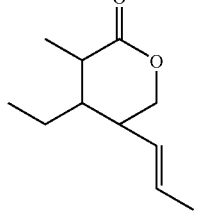
(VII)

(10) Further, the perfume composition of the present invention is a perfume composition which contains two or more compounds selected from the group consisting of the compounds represented by the following formulae (III) to (VII).

(11) Further, the perfume composition of the present invention is a perfume composition which contains a perfume of which main starting material is camphorenal.

(12) Further, the perfume composition of the present invention is a perfume composition according to any one of the above item (6) to (8), which contains one or more compounds selected from the group consisting of Component (A): 2-ethyl-4-(2,2,3-trimethyl-3-cyclopenten-1-yl)-2-buten-1-ol, 3-trimethyl-3-cyclopenten-1-yl)-2-buten-1-ol, 3-methyl-5-(2,2,3-trimethyl-3-cyclopenten-1-yl)-pentan-2-ol, 2-methyl-4-(2,2,3-trimethyl-3-cyclopenten-1-yl)-butanol, 3,3-dimethyl-5-(2,2,3-trimethyl-3-cyclopenten-1-yl)-4-penten-2-ol, 3-methyl-5-(2,2,3-trimethyl-3-cyclopenten-1-yl)-4-penten-2-ol, 2-methyl-4-(2,2,3-trimethyl-3-cyclopenten-1-yl)-2-buten-1-ol and optical isomers thereof.

The present invention relates to:

(13) a household product containing the perfume composition according to any one of the above items (6) to (12),

(14) a personal care and cosmetic product containing the perfume composition according to any one of the above items (6) to (12),

(15) an environmental hygiene product containing the perfume composition according to any one of the above items (6) to (12),

(16) a beverage containing the perfume composition according to any one of the above items (6) to (12), and

(17) a food containing the perfume composition according to any one of the above items (6) to (12).

BEST MODE FOR CARRYING OUT THE INVENTION

Figure 1:
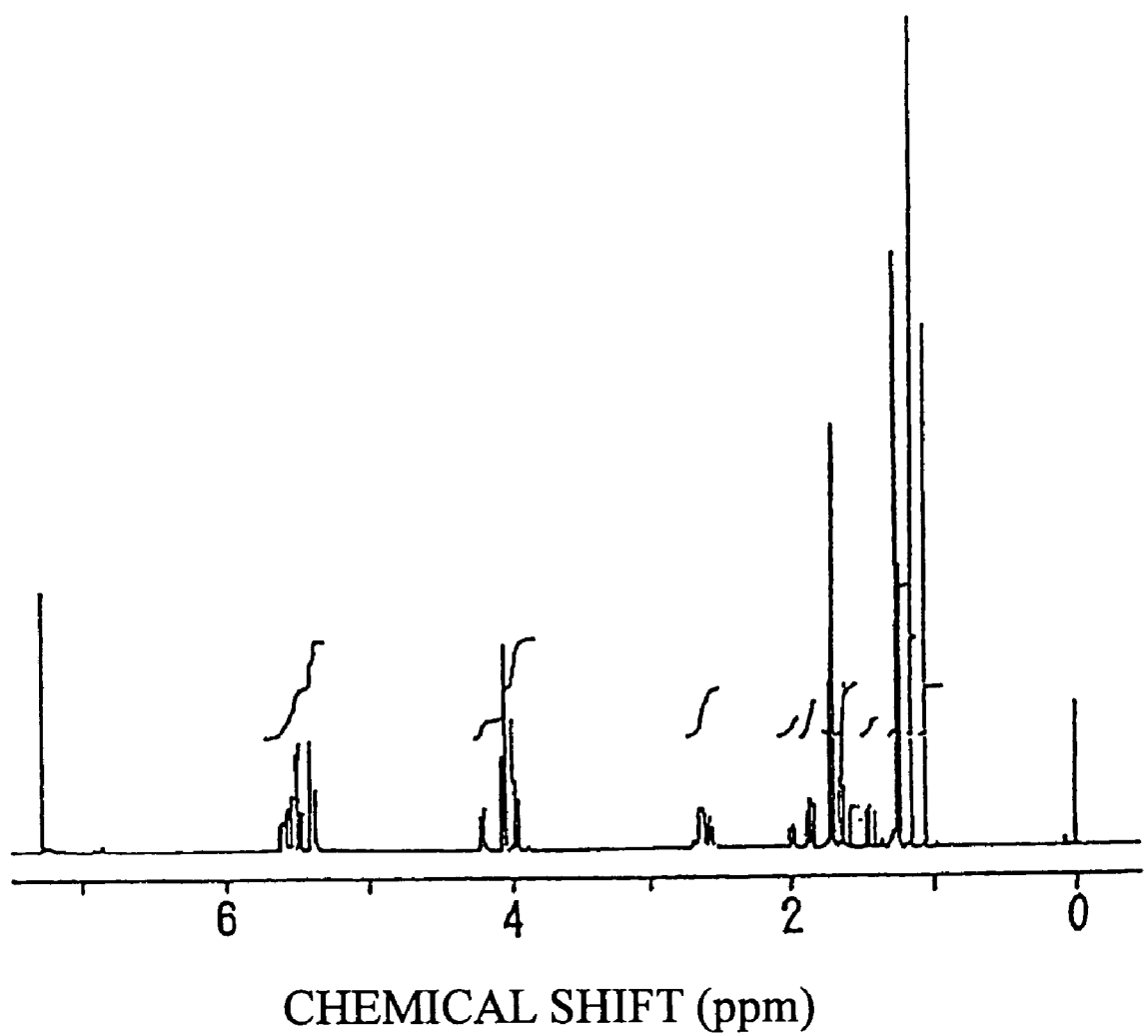
FIG. 1 is an $^1$H-NMR (400 MHz) chart of α-methyl-γ-methyl-γ-1-propenyl-valerolactone.

The valerolactone compound of the present invention is represented by the formula (I), and has a sweet odor useful as a perfume substance.

Among the compounds resented by the formula (I), α-methyl-γ-ethyl-γ-methyl-γ-1-propenyl-δ-valerolactone resented by the formula (II) is especially preferable since this compound itself has both a woodsy odor and a coumarin-like sweet odor which reminds of tonka beans, and is easily harmonized with a woodsy perfume. In other words, when a perfume composition is prepared by combining the valerolactone compound represented by the formula (II) with a woody perfume, a soft and sweet milk-like odor harmonized with a woody odor can be exhibited.

Especially, when the valerolactone compound represented by the formula (II) is combined with a synthetic sandalwood-type aroma chemical, there can be provided an odor harmonized with the woody odor of the sandalwood-type aroma chemical, which has soft and sweet milk-like woody and balsamic odor, so that odor characteristics of natural sandalwood can be easily exhibited. Also, this valerolactone compound has an advantage such as long-lasting effect In addition, the valerolactone compound represented by the formula (I) is characterized in that the compound has an alkyl group on position α, β or γ except position δ. Most of valerolactones commonly used as a perfume have an alkyl substituent on position δ, and have a sweet coconut-like odor. The more the number of the carbon atoms is, the stronger the characteristic milk-like odor becomes, so that it is more likely to be used for food flavor due to its odor character.

On the other hand, the valerolactone compound represented by the formula (I) has a fragrance similar to the compound having an alkyl substituent on position δ and a unique woodsy fragrance which the δ-substituted compound does not have; nevertheless this compound does not have an alkyl substituent on position δ. Therefore, the valerolactone compound has an advantage that the compound is easily harmonized with various perfumes, for instance, perfumes used in household products such as detergents for clothes and softeners for clothes; personal care and cosmetic products such as soap, body soap, shampoo, cosmetics and perfumes; environmental hygiene products such as air fresheners, deodorants, incense sticks and candles; and the like.

In other words, since an alkyl substituent is introduced into the valerolactone on either position α, β or γ, a compound having various characteristic odor such as a woody odor, a spicy odor and a floral odor together with a sweet odor can be synthesized. Furthermore, since an unsaturated bond is introduced into the valerolactone, the odor becomes stronger and gives various odor.

For instance, the compound represented by the formula (III) has both a woody and a spicy odor, and emits a novel and strong odor which reminds of costus and iris.

The compound represented by the formula (IV) has both a woody odor and floral odor. In addition, this compound has a novel and soft fragrance as compared to the compound represented by the formula (III).

The compound represented by the formula (V) has a cedarwood-like woody odor and a coumarin-like sweet odor.

The compound represented by the formula (VII) has both a woody odor and a green odor. Also, this compound has a novel odor which reminds of sandalwood, although this fragrance is slightly weaker than that of the compound represented by the formula (II).

Each of the valerolactone compounds represented by the formula (I) can be included alone in the perfume composition, respectively. Alternatively, the valerolactone compounds can be used in combination with two or more kinds. For instance, when two or more compounds selected from the group consisting of the compounds represented by the formula (II), the compounds represented by the formula (III), the compounds represented by the formula (IV), the compounds represented by the formula (V), the compounds represented by the formula (VI) and the compounds represented by the formula (VII) are used in combination, various odor having odor characters and various strength of odor, such as a woody odor, a floral odor, a spicy odor and a costus odor can be imparted to the compound. In addition, such combination has an advantage that the odor can be more easily matched with the uses of the fragrances as compared with the single use of the compound.

The compound represented by the formula (V) has a woody odor and a novel coumarin-like sweet odor. The combination of the compound represented by the formula (V) with the compound represented by the formula (II) is especially suitable for the use as a substitute for a coumarin.

The valerolactone compound represented by the formula (I) can be synthesized, for instance, via a route as shown in the Scheme 1.

More specifically, an alkaline condensation reaction of an acrylonitrile derivative with a malonic acid ester derivative is carried out in the presence of an alkali such as sodium methoxide. Subsequently, the resulting compound A can be converted to a compound B with a hydride reducing reagent such as lithium borohydride ($LiBH_4$). Thereafter, the nitrile moiety is hydrolyzed in the presence of an alkali (an aqueous solution of sodium hydroxide and the like), and the resulting product is treated with an acid such as sulfuric acid, to synthesize a hydroxyvalerolactone C. The hydroxyl group of this compound is oxidized with an oxidizing agent such as pyridinium dichromate (PDC), to give an aldehyde D. The number of carbon atoms in the aldehyde is increased by Wittig reaction, and the resulting olefin is isomerized, to synthesize a compound F. In addition, the compound F' can be easily synthesized from the olefin having a side chain on position γ by treating the olefin with hydrogen using a hydrogenation catalyst such as palladium/carbon (Pd/C).

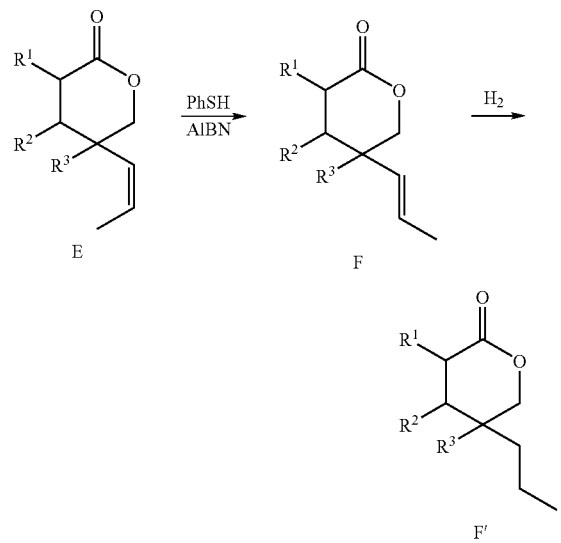

Also, a compound in which $R^4$ is a phenyl group can be synthesized via a route as shown in the Scheme 2. More specifically, a compound G can be synthesized by carrying out an alkaline condensation reaction of an acrolein derivative with an aldehyde, followed by carrying out the oxidation.

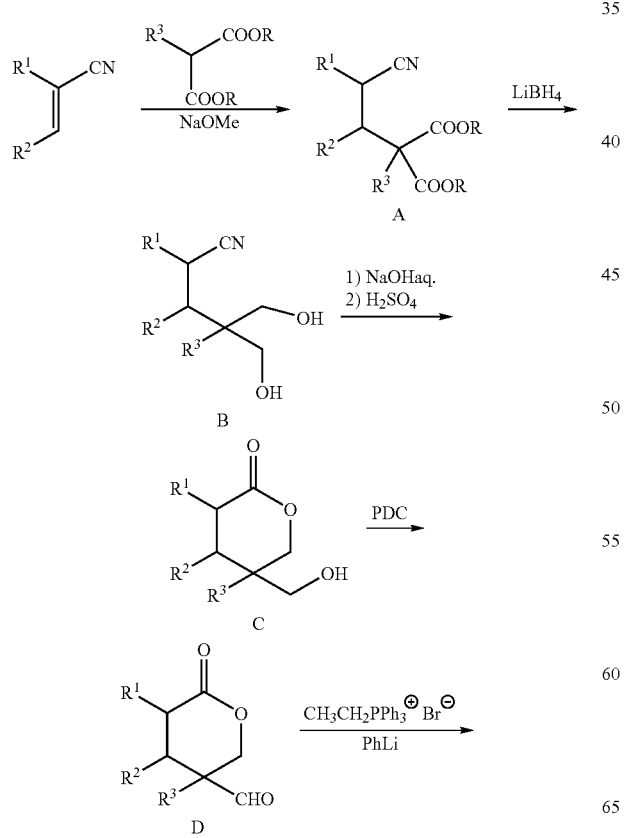

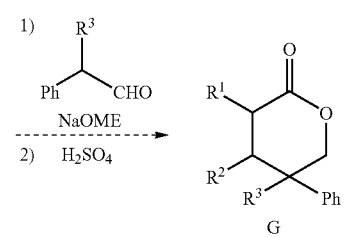

The valerolactone compound represented by the formula (II) can be synthesized, as shown in the Scheme 3, by using as a starting material, propanal represented by the formula (H) or 2-methyl-2-pentenal represented by the formula (J). In the scheme, X represents a hydrogen atom or a metal atom. The metal atom includes alkali metal atoms such as a potassium atom and a sodium atom, alkaline earth metal atoms such as a calcium atom and a magnesium atom, and the like. When the metal atom is an alkaline earth metal atom, X in the compound represented by the formula (L) is read as X/2.

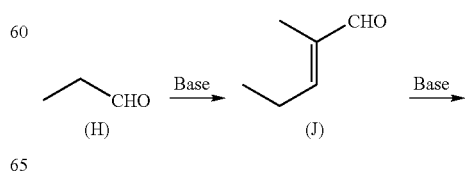

-continued

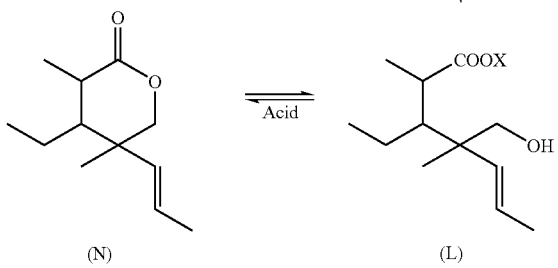

More specifically, the compound represented by the formula (K) and the compound represented by the formula (L) are sequentially prepared by treating propanal represented by the formula (H) or 2-methyl-2-pentenal represented by the formula (J) with a base. The resulting reaction solution is treated with an acid to react the —COOX group with the —OH group in the compound represented by the formula (L) to form a ring closure, and thereby the valerolactone compound represented by the formula (N) is prepared.

First, propanal or 2-methyl-2-pentenal is treated with a base. In this case, propanal or 2-methyl-2-pentenal can be treated with a base in a solvent.

The solvent is preferably a polar solvent from the viewpoint of enhancing the reactivity. For instance, lower alcohols having 1 to 3 carbon atoms, such as methanol, ethanol and isopropanol, and water are preferable. Among them, the combined use of water and a lower alcohol is preferable.

The amount of the solvent is preferably 0 to 1000 parts by weight, more preferably 50 to 700 parts by weight, even more preferably 100 to 500 parts by weight, based on 100 parts by weight of propanal or 2-methyl-2-pentenal, from the viewpoint of increasing the yield and enhancing the reactivity.

The base includes alkali metal hydroxides such as potassium hydroxide and sodium hydroxide, and alkaline earth metal hydroxides such as calcium hydroxide and magnesium hydroxide, alkali metal salts of a lower alcohol having 1 to 3 carbon atoms, such as potassium methoxide and sodium methoxide, and the like. Among them, one or more bases selected from the group consisting of potassium hydroxide, sodium hydroxide, potassium methoxide and sodium methoxide are preferable.

The amount of the base is preferably 0.001 to 10 mol, more preferably 0.005 to 5 mol, even more preferably 0.01 to 1 mol, per one mol of propanal or 2-methyl-2-pentenal.

As a method for treating propanal or 2-methyl-2-pentenal with a base, there can be cited, a method including mixing propanal or 2-methyl-2-pentenal with a base, for instance, a method including previously dissolving a base in a solvent and adding propanal or 2-methyl-2-pentenal to the resulting solution, a method including previously dissolving propanal or 2-methyl-2-pentenal in a solvent and adding a base or a solution thereof to the resulting solution, and the like.

The atmosphere in which propanal or 2-methyl-2-pentenal is treated with the base is not limited to specified ones. The atmosphere is preferably an atmosphere of an inert gas such as nitrogen gas or argon gas. The temperature at which propanal or 2-methyl-2-pentenal is treated with the base is not limited to specified ones. The temperature may be usually 20° to 60° C.

The end point for treating propanal or 2-methyl-2-pentenal with the base can be regarded as the time when propanal or 2-methyl-2-pentenal has disappeared as confirmed by, for instance, gas chromatography, thin layer chromatography or the like. The time period required for the treatment of propanal or 2-methyl-2-pentenal with the base cannot be absolutely determined since the time period varies depending on the reaction conditions. The time period is usually 1 to 48 hours or so.

Next, the reaction solution obtained is treated with an acid to give a valerolactone compound.

It is preferable that water and an ether are added to the reaction solution, the resulting solution is stirred and allowed to separate into an aqueous layer and an ether layer, and the aqueous layer is taken out from the solution by removing the ether layer to use the aqueous layer in the acid treatment, prior to the treatment of the reaction solution with an acid.

In this case, as the ether, those commonly used such as diethyl ether can be used. The amounts of water and the ether are not limited to specified ones. Each amount of water and the ether is preferably 50 to 200 parts by weight based on 100 parts by weight of the reaction solution, respectively.

The acid includes inorganic acids such as hydrochloric acid and phosphoric acid; and organic acids such as acetic acid, citric acid and tartaric acid. Among them, inorganic acids are preferable.

The treatment of the reaction solution with the acid can be usually carried out by adding the acid to the reaction solution (aqueous layer) so that the pH of the reaction solution (aqueous layer) is 1 to 6, preferably 2 to 4, to make the solution acidic. During this treatment, the liquid temperature of the reaction solution is not limited to specified ones, and may be usually 5° to 40° C or so. The end point of the acid treatment can be regarded as the time point when the pH of the reaction solution is included in the above-mentioned range, as determined by using a pH test paper (for instance, commercially available from Merck under the trade name of Acilit pH 0 to 6).

The valerolactone compound of the present invention is contained in the reaction mixture thus obtained by the acid treatment. The valerolactone compound can be isolated by adding, for instance, an ether to the reaction mixture to extract a crude product, and thereafter purifying the crude product by the use of silica gel chromatography or the like.

The perfume composition of the present invention contains the valerolactone compound represented by the formula (I). The valerolactone compound represented by the formula (I) is a compound having a novel odor. Therefore, various novel odor can be easily created by combining this compound with various fragrances.

Examples of perfume substances which can be used in combination with the valerolactone compound of the present invention include the followings:

hydrocarbons such as limonene, α-pinene, β-pinene, terpinene, cedrene, longifolene and valencene;

alcohols such as linalool, citronellol, geraniol, nerol, terpineol, dihydromyrcenol, ethyl linalool, famesol, nerolidol, cis-3-hexenol, cedrol, menthol, borneol, phenyl ethyl alcohol, benzyl alcohol, phenyl hexanol, 2,2,6-trimethyl cyclohexyl-3-hexanol and 1-(2-t-butyl cyclohexyloxy)-2-butanol;

phenols such as eugenol, thymol and vanillin;

ethers such as linalyl formate, citronellyl formate, geranyl formate, n-hexyl acetate, cis-3-hexenyl acetate, linalyl acetate, citronellyl acetate, geranyl acetate, neryl acetate, terpinyl acetate, nopyl acetate, bornyl acetate, isobornyl acetate, o-t-butylcyclohexyl acetate, p-t-butylcyclohexyl acetate, tricyclodecenyl acetate, benzyl acetate, styrallyl acetate, cinnamyl acetate, dimethylbenzylcarbinyl acetate, 3-pentyltetrahydropyran-4-yl acetate, citronellyl propionate, tricyclodecenyl propionate, allylcyclohexyl propionate, ethyl 2-cyclohexylpropionate, benzyl propionate, citronellyl butyrate, dimethylbenzylcarbinyl n-butyrate, tricyclodecenyl isobutyrate, methyl 2-nonenoate, methyl benzoate, benzyl benzoate, methyl cinnamate, methyl salicylate, n-hexyl salicylate, cis-3-hexenyl salicylate, cyclohexyl salicylate, geranyl tiglate, cis-3-hexenyl tiglate, methyl jasmonate, methyl dihydrojasmonate, methyl 2,4-dihydroxy-3,6-dimethyl benzoate, ethylmethylphenyl glycidate, methyl anthranilate, and FRUITATE (trade name, commercially available from Kao Corporation);

aldehydes such as n-octanal, n-decanal, n-dodecanal, 2-methylundecanal, 10-undecenal, citronellal, citral, hyroxycitronellal, dimethyltetrahydrobenz-aldehyde, 4(3)-(4-hydroxy-4-methylpentyl)-3-cyclohexene-1-carboaldehyde, 2-cyclohexylpropanal, p-t-butyl-α-methylhydrocinnamic aldehyde, p-isopropyl-α-methylhydrocinnamic aldehyde, p-ethyl-α,α-dimethylhydrocinnamic aldehyde, α-amylcinnamic aldehyde, α-hexylcinnamic aldehyde, piperonal, and α-methyl-3,4-methylenedioxyhydrocinnamic aldehyde;

ketones such as methyl heptenone, 4-methylene-3,5,6,6-tetramethyl 2-heptanone, amyl cyclopentanone, 3-methyl-2-(cis-2-penten-1-yl)-2-cyclopenten-1-one, methyl cyclopentenolone, rose ketone, γ-methylionone, α-ionone, carvone, menthone, camphor, acetyl cedrene, isolongifolanone, nootkatone, benzyl acetone, anisyl acetone, methyl β-naphthyl ketone, 2,5-dimethyl-4-hydroxy-3(2H)-furanone, maltol, muscone, civetone, cyclopentadecanone and cyclohexadecene;

acetals and ketals, such as formaldehyde cyclododecylethylacetal, acetaldehyde ethylphenylpropylacetal, citral diethylacetal, phenylacetaldehyde glycerinacetal and ethylacetacetate ethylene glycol ketal;

ethers such as cedryl methyl ether, anethole, β-naphthyl methyl ether, β-naphthyl ethyl ether, limonene oxide, rose oxide, 1,8-cineol and decahydro-3a,6,6,9a-tetramethylnaphtho[2.1-b]furan; and nitriles such as geranylnitrile and citronellylnitrile.

In addition to the carboxylic acids, there can be also used lactones such as γ-nonalactone, γ-undecalactone, δ-decalactone, γ-jasmolactone, coumarin, cyclopentadecanolide, cyclohexadecanolide, ambrettolide, ethylene brassylate and 1-oxahexadecanolide; natural essential oils and natural extracts of orange, lemon, bergamot, mandarin, peppermint, spearmint, lavender, chamomile, rosemary, eucalyptus, sage, basil, rose, geranium, jasmine, ylang-ylang, anis, clove, ginger, nutmeg, cardamom, cedar, Japanese cypress, vetiver, patchouli, labdanum, and the like.

The valerolactone compound of the present invention represented by the formula (I) can be arbitrarily combined with the above-mentioned perfume substances. The content of the valerolactone compound in the perfume is not limited to specified ones. The content is usually at least 0.001% by weight, preferably at least 0.01% by weight, more preferably at least 0.2% by weight, still more preferably at least 0.3% by weight, even more preferably at least 0.4% by weight, most preferably at least 0.5% by weight, from the viewpoint of providing a unique sweet and woody odor.

A perfume having a sandalwood-like odor is especially suitable for use as odor to be combined with the valerolactone compound represented by the formula (II) since the perfume provides a perfume composition having a high quality such as a natural sandalwood-like odor.

Examples of the perfumes having a sandalwood-like odor include the following synthetic perfumes (B):

(B) one or more compounds selected from the group consisting of perfumes of which main starting material is camphorenal such as 2-methyl-4-(2,2,3-trimethyl-3-cyclopenten-1-yl)-2-buten-1-ol, 2-ethyl-4-(2,2,3-trimethyl-3-cyclopenten-1-yl)-2-buten-1-ol, 3-methyl-5-(2,2,3-trimethyl-3-cyclopenten-1-yl)-pentan-2-ol, 2-methyl-4-(2,2,3-trimethyl-3-cyclopenten-1-yl)-butanol, 3,3-dimethyl-5-(2,2,3-trimethyl-3-cyclopenten-1-yl)-4-penten-2-ol and 3-methyl-5-(2,2,3-trimethyl-3-cyclopenten-1-yl)-4-penten-2-ol; isocamphylcyclohexanols; and 3,7-dimethyl-7-methoxyoctan-2-ol; and optical isomers of each compound mentioned above.

Among the above-mentioned synthetic perfumes (B), preferable are the following components (A):

(A) one or more compounds selected from the group consisting of: 2-ethyl-4-(2,2,3-trimethyl-3-cyclopenten-1-yl)-2-buten-1-ol, 3-methyl-5-(2,2,3-trimethyl-3-cyclopenten-1-yl)-pentan-2-ol, 2-methyl-4-(2,2,3-trimethyl-3-cyclopenten-1-yl)-butanol, 3,3-dimethyl-5-(2,2,3-trimethyl-3-cyclopenten-1-yl)-4-penten-2-ol, 3-methyl-5-(2,2,3-trimethyl-3-cyclopenten-1-yl)-4-penten-2-ol and 2-methyl-4-(2,2,3-trimethyl-3-cyclopenten-1-yl)-2-buten-1-ol, and optical isomers of these compounds.

The compound represented by the formula (I) and the above-mentioned perfume having a sandalwood-like odor can be arbitrarily combined. The weight ratio of the valerolactone compound to the above-mentioned odor (B) having a sandalwood-like odor is not limited to specified ones. The weight ratio is preferably at least 1:100000, more preferably at least 1:10000, even more preferably at least 1:1000, from the viewpoint of providing a unique soft and sweet milk-like fragrance which is a characteristic of natural sandalwood. Also, the above-mentioned weight ratio is preferably 1:100000 to 1:1, more preferably 1:1000 to 3:7, still more preferably 1:1000 to 2:8, even more preferably 1:500 to 1:9, most preferably 1:350 to 1:9.

The perfume composition of the present invention can be prepared by mixing the above-mentioned valerolactone compound with the other perfume by a known method. The perfume composition containing the valerolactone compound can be used in or added to fragrant products having various forms. The fields to which the perfume composition of the present invention can be applied include, for instance, household products, personal care and cosmetic products, environmental hygiene products and the like.

The household products are ones for maintaining the functions and cleanness of homes and various products such as household commodities necessary for home life. Specifically, the household products include detergents for clothes, softeners for clothes, house cleaner, bathroom cleaner, dishwashing detergents, bleaching agents, mildew cleaners, floor waxes and the like. The perfume composition of the present invention can be formulated in any amounts for these goods. The amount of the perfume composition is usually 0.001 to 2% by weight, preferably 0.01 to 1% by weight.

The personal care and cosmetic products are ones for keeping a person clean or beautifying a person. Specifically, the personal care and cosmetic products include soap, body shampoo, shampoo, hair care products, cosmetics (for instance, skin care products, make-up and the like), perfumes, eau de colognes, antiperspirants, deodorants, bath additives, and the like. The perfume composition of the present invention can be used in an arbitrary amount for these goods. For instance, the content of the perfume composition of the present invention in these goods is 0.0001 to 50% by weight. The content is preferably 1 to 40% by weight in the case of perfumes and eau de colognes, and 0.001 to 2% by weight in the case of the goods other than perfumes and eau de colognes, such as soap, body soap, shampoo, hair care products, cosmetic antiperspirants, deodorants and bath additives.

Also, the environmental hygiene products are ones for controlling the environment to a desired condition or atmosphere. Particular goods containing the perfume composition, capable of controlling the fragrance emitted to the environment include air freshener, deodorants, incense, incense sticks, candles and the like. The perfume composition of the present invention can be used in an arbitrary amount in the group of these products. For instance, the content of the perfume composition of the present invention in the goods is 0.01 to 80% by weight, preferably 0.1 to 70% by weight.

Moreover, the valerolactone compound of the present invention can be used as a flavor used in foods and beverages. The valerolactone compound can impart characteristic sweet flavor to coffee beverages, liquors, bakery, daily products and the like, for instance, by adding the valerolactone compound. Furthermore, the valerolactone compound of the present invention can be also used as a flavor for oral care products (for instance, toothpaste, mouthwash and the like) and flavors for cigarettes.

The products containing the perfume composition can be used in various methods, for instance, a method for applying perfume or cosmetics to a desired portion of a body to aggressively emit its fragrance; a method for washing clothes with a detergent to allow its fragrance to be left on the clothes after washing; a method for spreading the fragrance in the air by volatilizing the odor from air fresheners; a method for spreading the fragrance in the air by burning an incense stick or candle, and the like.

In one embodiment, it is possible to impart characteristic soft and sweet odor like natural sandalwood to clothes to leave its odor remaining in the clothes by adding a perfume composition containing 1% by weight of the valerolactone compound and optionally a sandalwood-type aroma chemical to a softener for clothes in amount of 0.1% by weight of the softener.

EXAMPLES

Next, the present invention is more specifically explained on the basis of examples. However, the present invention is not intended to be limited to these examples.

Example 1

Synthesis of α-methyl-γ-methyl-γ-1-propenylvalerolactone

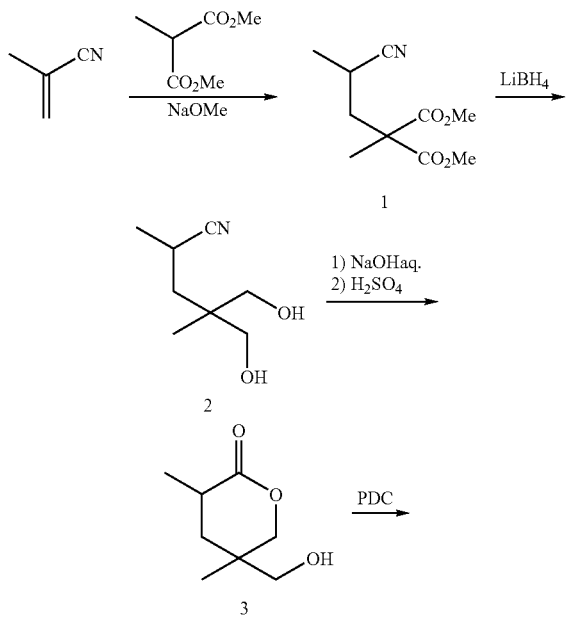

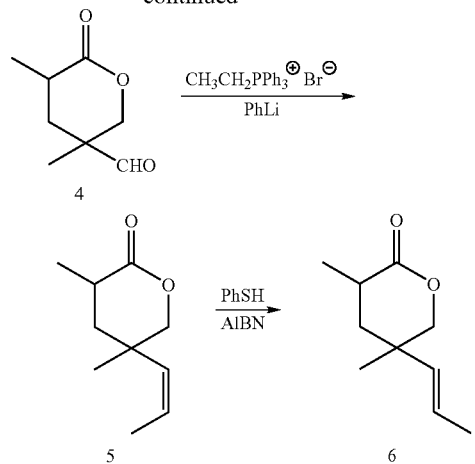

A 200 mL four-neck flask was charged with 20.13 g (0.300 mol) of methacrylonitrile, 52.26 g (0.300 mol) of diethyl methylmalonate and 2.35 mL (0.006 mol) of a 20% sodium ethoxide solution in ethanol, and the mixture was reacted at 90° C. for 12 hours. A buffer having a pH of 6.86 was added to neutralize, and washed with saturated saline to give 72.0 g of a crude product (1).

(2) Reduction, Hydrolysis and Cyclization Reactions

A 500 mL four-neck flask was charged with dehydrated tetrahydrofuran (200 mL), and stirred. The flask was charged with 6.36 g (0.290 mol) of lithium borohydride at room temperature. The reaction solution was cooled to −60° C., and the crude product (1) was added dropwise thereto over 10 minutes. The temperature of the reaction solution was gradually raised, followed by a reaction at 0° C. for 3 hours. 10% sulfuric acid (100 mL) was slowly added dropwise to the reaction solution while maintaining at 0° C., to adjust the pH of the reaction solution to 4. The temperature of the reaction solution was raised to room temperature, and an aqueous sodium hydroxide solution (sodium hydroxide 37.0 g, distilled water 100 mL) was added thereto slowly.

A Dean Stark tube was attached to the flask, and the temperature of the reaction solution was raised to 85° C. to remove tetrahydrofuran from the reaction system, followed by a reaction at this temperature for 2.5 hours. The reaction solution was transferred to a separatory funnel, and washed with diethyl ether three times. 6N hydrochloric acid was added to the aqueous layer to adjust the pH to 2. The aqueous layer was extracted with ethyl acetate six times. The organic layers were combined, and dried with sodium sulfate. The solvent was removed under reduced pressure to give 38.14 g of a crude product (3). Purification by silica gel column chromatography (hexane:ethyl acetate=2: 8 (volume ratio)) afforded 13.35 g of an intermediate product (3).

(3) Oxidation Reaction

A one liter four-neck flask was charged with dehydrated methylene chloride (400 mL), 13.35 g (0.084 mol) of the intermediate product (3) and 31.75 g (0.084 mol) of pyridinium dichromate, and the mixture was reacted at room temperature for 22 hours. Diethyl ether was added to the resulting reaction solution, and the reaction solution was filtered with silica gel to give 10.31 g of a crude product. Purification by silica gel column chromatography (hexane ethyl acetate=1:1 (volume ratio)) afforded 5.60 g of an intermediated product (4).

(4) Wittig Reaction

A 300 mL four-neck flask was charged with dehydrated tetrahydrofuran (19 mL) and 11.41 g (0.030 mol) of ethyltriphenyl phosphonobromide, and the mixture was stirred at room temperature. To the flask was added 32.7 mL (0.030 mol) of a 0.94M phenyl lithium solution in toluene and cyclohexane, the mixture was stirred at room temperature for 30 minutes, and thereafter cooled to −30° C. A dehydrated tetrahydrofuran (12.5 mL) solution containing 4.80 g (0.03 mol) of the intermediated product (4) was added dropwise to the flask over 50 minutes, and the temperature was raised to room temperature, followed by stirring at room temperature for 10 minutes. An aqueous saturated ammonium chloride solution (10 mL) and 0.1N hydrochloric acid (40 mL) were added to the reaction solution. The reaction solution was extracted with diethyl ether three times, and washed with an aqueous saturated sodium hydrogencarbonate solution and a buffer having a pH of 6.86 once, respectively. The solvent was removed from the solution under reduced pressure to give 3.20 g of a crude product. Purification by silica gel column chromatography (hexane:ethyl acetate=8:2 (volume ratio)) afforded 122.0 mg of an intermediate product (5).

(5) Isomerization Reaction

A 100 mL four-neck flask was charged with 588.7 mg (0.527 mmol) of the intermediate product (5), 29.0 mg (0.264 mmol) of thiophenol, 13.0 mg (0.079 mmol) of 2,2'-bisazoisobutyronitrile and benzene (15 mL), and the mixture was reacted at 80° C. After the reaction for 2 hours, 13.0 mg (0.079 mmol) of 2,2'-bisazoisobutyronitrile was added again. After a further reaction for 2 hours, 13.0 mg (0.079 mmol) of azoisobutyronitrile was added again, and the reaction was terminated after 2 hours. The solvent was removed from the solution under reduced pressure, and the crude product was purified by silica gel column chromatography (hexane:ethyl acetate)=8:2 (volume ratio)) to give 30.2 mg of an end product (6).

Example 2

Synthesis of β-ethyl-γ-methyl-γ-1-propenylvalerolactone

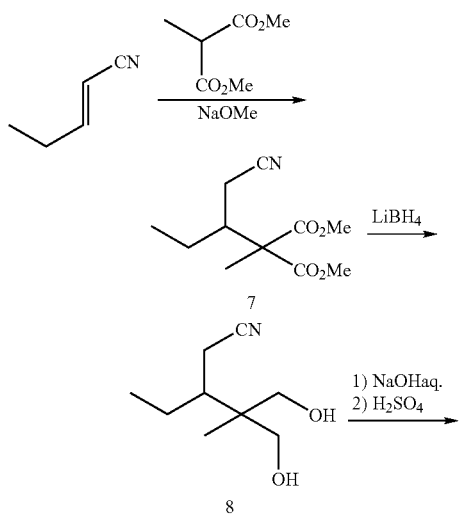

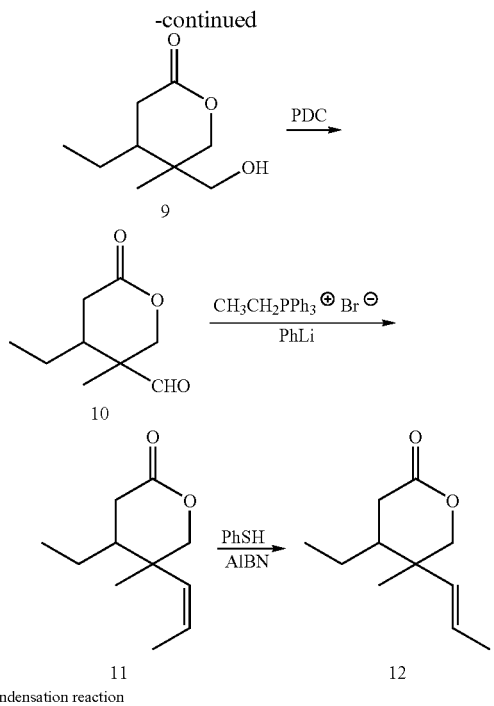

(1) Alkali condensation reaction

A 100 mL four-neck flask was charged with 20.60 g (0.254 mol) of 2-pentenitrile, 41.30 g (0.283 mol) of dimethyl methylmalonate and 2.60 mL (0.127 mol) of 28% sodium methoxide solution in methanol, and the mixture was reacted at 130° C. for 7 hours. A buffer having a pH of 6.86 was added to the reaction solution to neutralize, and washed with saturated saline to give 36.0 g of a crude product (7).

(2) Reduction, Hydrolysis and Cyclization Reactions

A 500 mL four-neck flask was charged with dehydrated tetrahydrofuran (100 mL), and stirred. The flask was charged with 3.52 g (0.162 mol) of lithium borohydride at room temperature. The reaction solution was cooled to −60° C., and the crude product (7) was added dropwise to the solution over 10 minutes. The temperature of the reaction solution was gradually raised, followed by a reaction at 30° C. for 3 hours. The reaction solution was cooled to 0° C. again, and 10% sulfuric acid (65 mL) was gradually added dropwise to the solution to adjust the pH of the solution to 2. The temperature was raised to room temperature, and an aqueous sodium hydroxide solution (sodium hydroxide 20.0 g, distilled water 80 mL) was added to the solution slowly.

A Dean Stark tube was attached to the flask, and the temperature of the reaction solution was raised to 97° C. to remove tetrahydrofuran from the reaction system, followed by a reaction at this temperature for 2.5 hours. The reaction solution was transferred to a separatory funnel, and washed with diethyl ether three times. To the aqueous layer was added 6N hydrochloric acid to adjust the pH to 2, and extracted with ethyl acetate six times. The organic layers were combined, and dried with sodium sulfate. The solvent was removed under reduced pressure to give 25.13 g of a crude product (9). Purification by silica gel column chromatography (hexane:ethyl acetate=3:7 (volume ratio)) afforded 12.85 g of an intermediate product (9).

(3) Oxidation Reaction

A one liter four-neck flask was charged with dehydrated methylene chloride (400 mL), 12.85 g (0.075 mol) of the intermediate product (9) and 28.07 g (0.075 mol) of pyridinium dichromate, and the mixture was reacted at room temperature for 17 hours. To the flask was added diethyl ether, and the reaction solution was filtered with silica gel to give 11.13 g of a crude product. Purification by Kugel Rohr distillation afforded 7.17 g of an intermediate product (10).

(4) Wittig Reaction

A 100 mL four-neck flask was charged with dehydrated tetrahydrofuran (30 mL) and 6.54 g (0.018 mol) of ethyltriphenyl phosphonobromide, and the mixture was stirred at room temperature. To the flask was added 18.7 mL (0.018 mol) of a 0.94M phenyllithium solution in toluene and cyclohexane. The mixture was stirred at room temperature for 30 minutes, and cooled to −50° C. A dehydrated tetrahydrofruan (20 mL) solution containing 3.00 g (0.018 mol) of the intermediate product (10) was added dropwise to the solution over 20 minutes, and the temperature was raised to room temperature, followed by stirring at room temperature for 10 minutes. An aqueous saturated ammonium chloride solution (10 mL) and 0.1M hydrochloric acid (40 mL) were added to the reaction solution. The reaction solution was extracted with diethyl ether three times, and washed with an aqueous saturated sodium hydrogencarbonate solution and a buffer having a pH of 6.86, respectively. The solvent was removed from the solution under reduced pressure to give 2.20 g of a crude product. Purification by silica gel column chromatography (hexane: ethyl acetate=9:1 (volume ratio)) afforded 240.0 mg of an intermediated product (11).

(5) Isomerization Reaction

A 100 mL four-neck flask was charged with 100.0 mg (0.550 mmol) of the intermediate product (11), 30.2 mg (0.274 mmol) of thiophenol, 13.5 mg (0.083 mmol) of 2,2'-bisazoisobutyronitrile and benzene (17 mL), and the mixture was reacted at 80° C. After the reaction for 2 hours, 13.5 mg (0.083 mmol) of 2,2'-bisazoisobutyronitrile was added again. After a further reaction for 2 hours, 13.5 mg (0.083 mmol) of azoisobutyronitrile was added again, and the reaction was terminated after 2 hours. The solvent was removed from the solution under reduced pressure, and the crude product was purified by silica gel column chromatography (hexane:ethyl acetate=8:2 (volume ratio)) to give 50.7 mg of an end product (12).

Example 3

Synthesis of α-methyl-β-ethyl-γ-methyl-γ-phenylvalerolactone

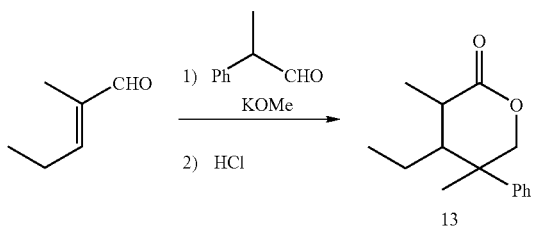

13

A 100 mL four-neck flask was charged with 3.92 g (0.040 mol) of 2-methyl-2-pentenal, 10.74 g (0.080 mol) of 2-phenylpropanal and 20 mL of dehydrated methanol, and the mixture was stirred at 35° C. for 5 minutes. 2.81 g (0.040 mol) of potassium methoxide was divided into five portions, and added to the mixture over 30 minutes. The temperature of the reaction solution was raised to 60° C., followed by stirring for 18.5 hours. The reaction solution was washed with diethyl ether and hexane once, respectively, and 1N hydrochloric acid was added to the solution to adjust the pH to 2.

After extraction with diethyl ether and hexane once, respectively, the organic layers were combined, and washed with a buffer having a pH of 6.86, and the organic solvent was removed under reduced pressure to give 3.22 g of a crude product. Purification by silica gel column chromatography (hexane:ethyl acetate=1:1 (volume ratio)) afforded 1.32 g of an end product (13).

Figure 2:
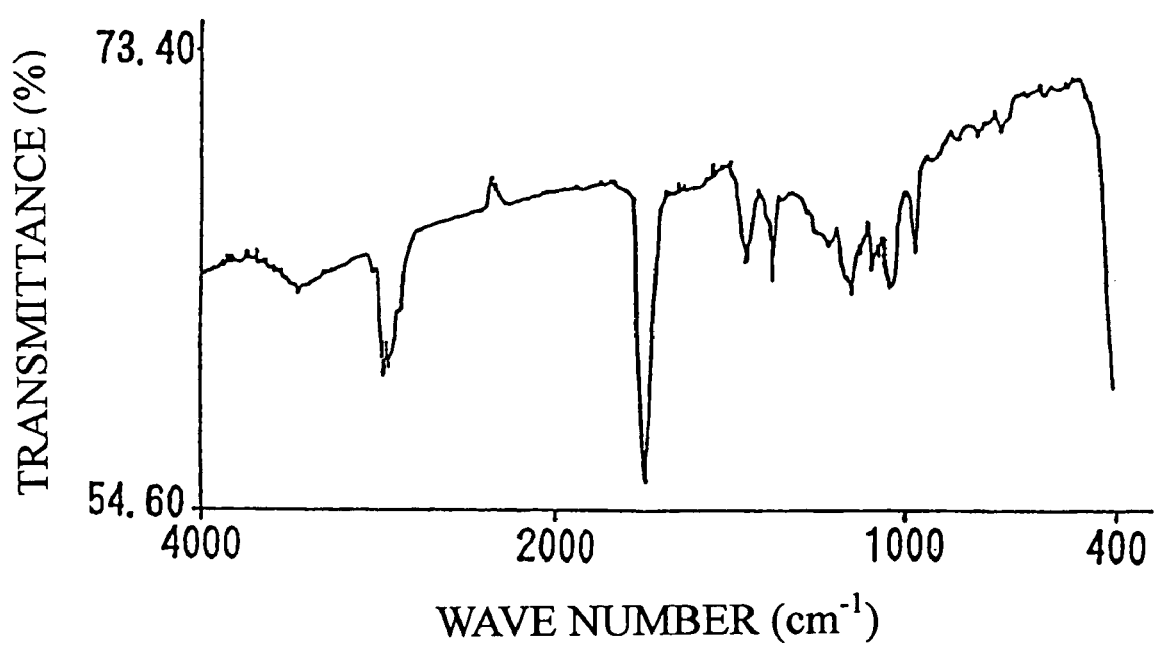
FIG. 2 is a graph showing the results of measurement of an infrared absorption spectrum of α-methyl-γ-methyl-γ-1-propenylvalerolactone.
Figure 3:
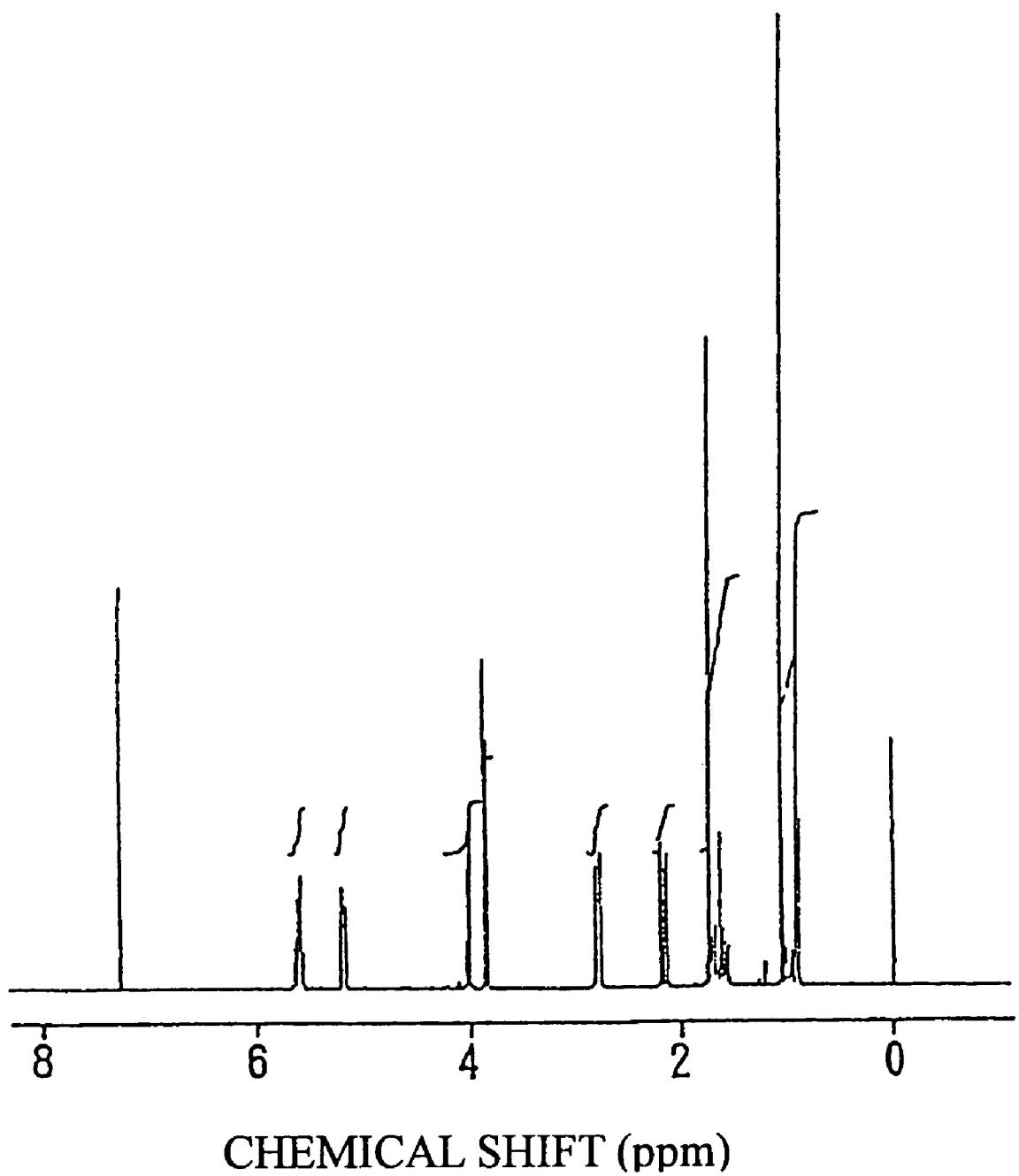
FIG. 3 is an $^1$H-NMR (400 Mz) chart of β-ethyl-γ-methyl-γ-1-propenyl-valerolactone.
Figure 4:
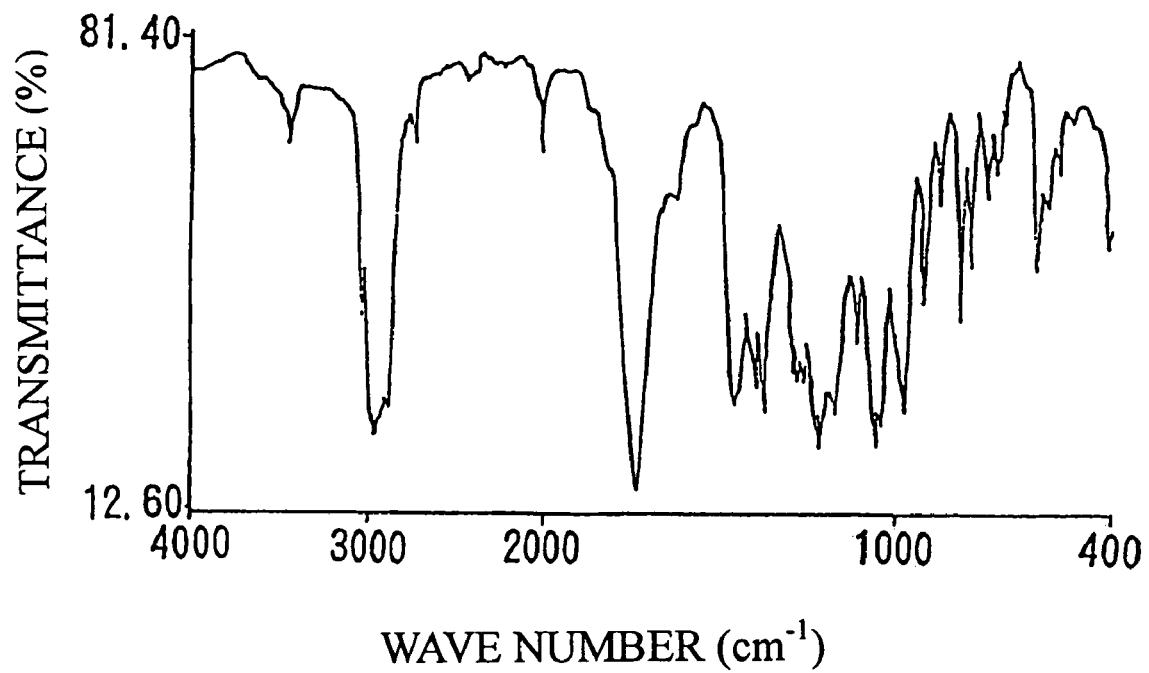
FIG. 4 is a graph showing the results of measurement of an infrared absorption spectrum of γ-ethyl-γ-methyl-γ-1-propenylvalerolactone.
Figure 5:
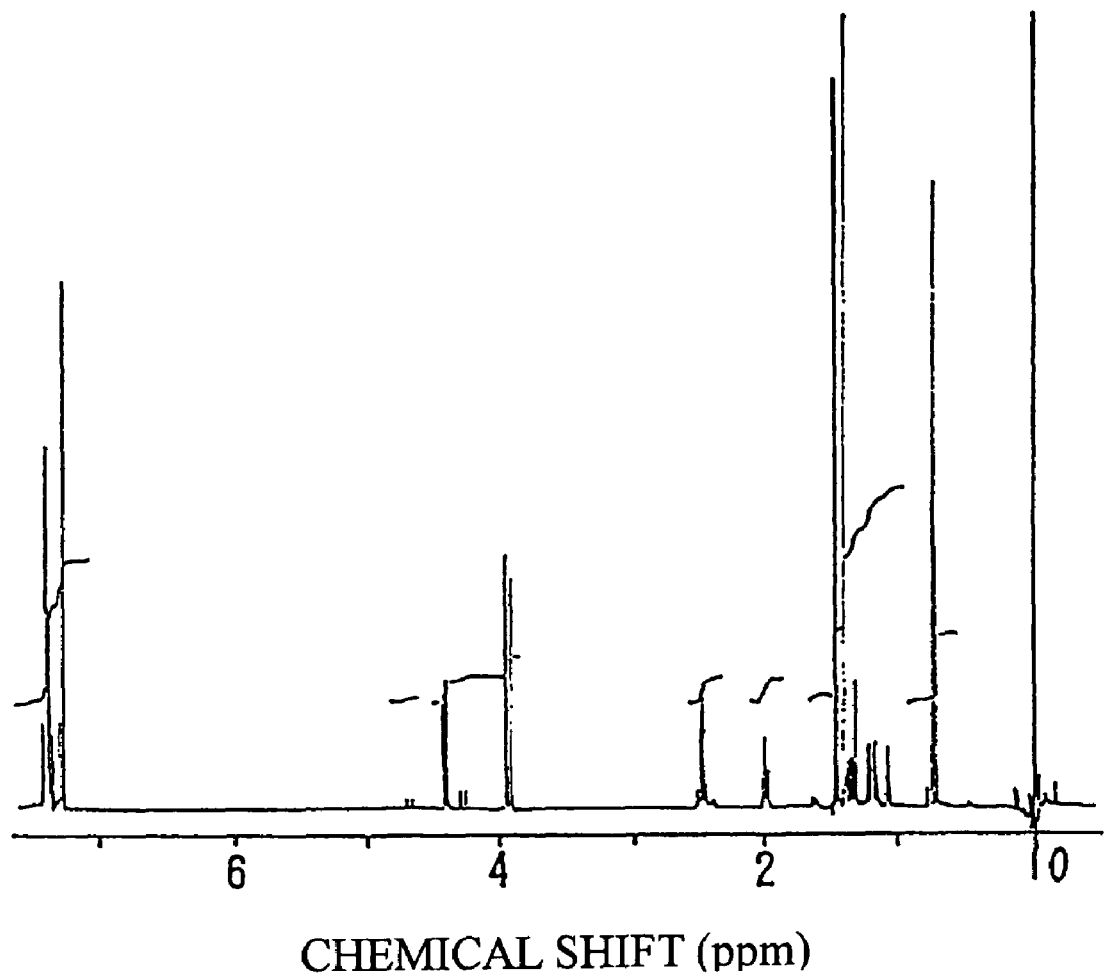
FIG. 5 is an $^1$H-NMR (400 MHz) chart of α-methyl-β-ethyl-γ-methyl-γ-phenyl-valerolactone.
Figure 6:
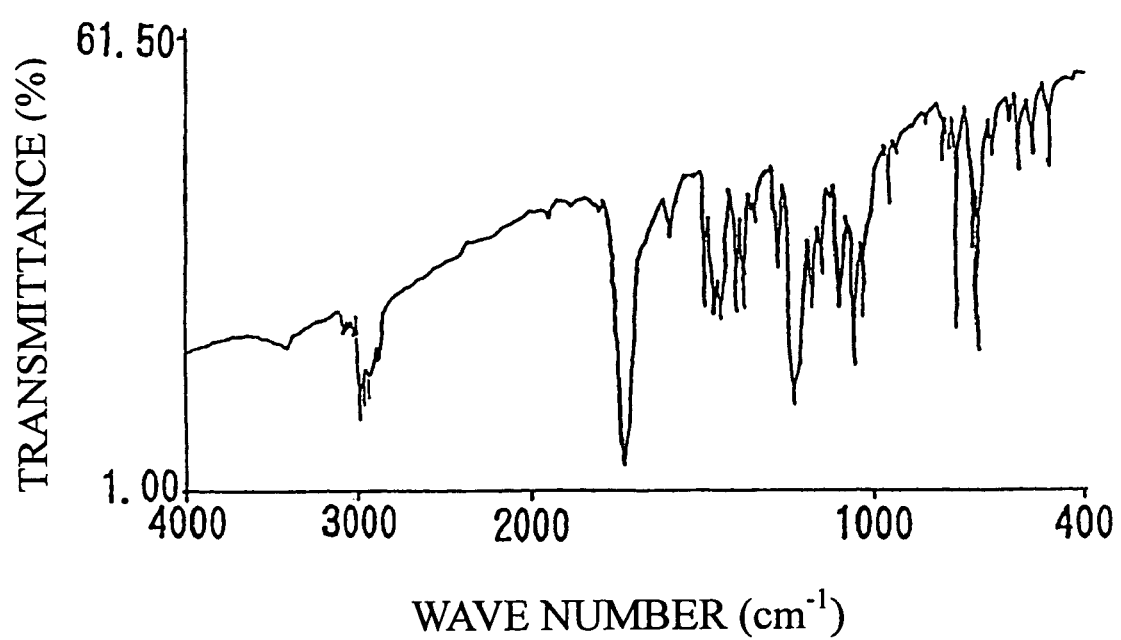
FIG. 6 is a graph showing the results of measurement of an infrared absorption spectrum of α-methyl-β-ethyl-γ-methyl-γ-phenylvalerolactone.

FIG. 1 shows an $^1$H-NMR (400 MHz) chart of α-methyl-γ-methyl-γ-1-propenyl-valerolactone. FIG. 2 shows an infrared adsorption spectrum (IR) chart of α-methyl-γ-methyl-γ-1-propenylvalerolactone. FIG. 3 shows an $^1$H-NMR (400 MHz) chart of β-ethyl-γ-methyl-γ-1-propenylvalerolactone. FIG. 4 shows an infrared absorption spectrum (IR) chart of β-ethyl-γ-methyl-γ-1-propenyl-valerolactone. FIG. 5 shows an $^1$H-NMR (400 MHz) chart of α-methyl-β-ethyl-γ-methyl-γ-phenylvalerolactone. FIG. 6 shows an infrared absorption spectrum (IR) chart of α-methyl-β-ethyl-γ-methyl-γ-phenyl-valerolactone.

Example 4

Synthesis of α-methyl-β-ethyl-γ-methyl-γ-1-propenyl-δ-valerolactone from propanal A 100 mL four-neck flask equipped with a stirrer and a thermometer was charged with 5.10 g of distilled water, 0.48 g of a 48% aqueous potassium hydroxide solution and 14.02 g of methanol, and the mixture was stirred at room temperature for 5 minutes. To the resulting solution was added dropwise 12.57 g of propanol over 1 minute. After completion of the addition, the temperature of the resulting solution was raised to 55° C., and heated to reflux for 46 hours.

Next, the resulting reaction solution was cooled to room temperature, and diluted with 100 mL of distilled water and 100 mL of diethyl ether to separate into layers. After the separation, the ether layer was removed, and hydrochloric acid was added to the aqueous layer to adjust the pH to 2, followed by extraction with 100 mL of diethyl ether two times. The resulting organic layers were combined. The solvent was distilled off under reduced pressure, and purified by silica gel column chromatography (hexane:ethyl acetate=4:1 (volume ratio)) to give 14.8 mg of α-methyl-β-ethyl-γ-methyl-γ-1-propenyl-6-valerolactone (yield 1.4%).

Figure 7:
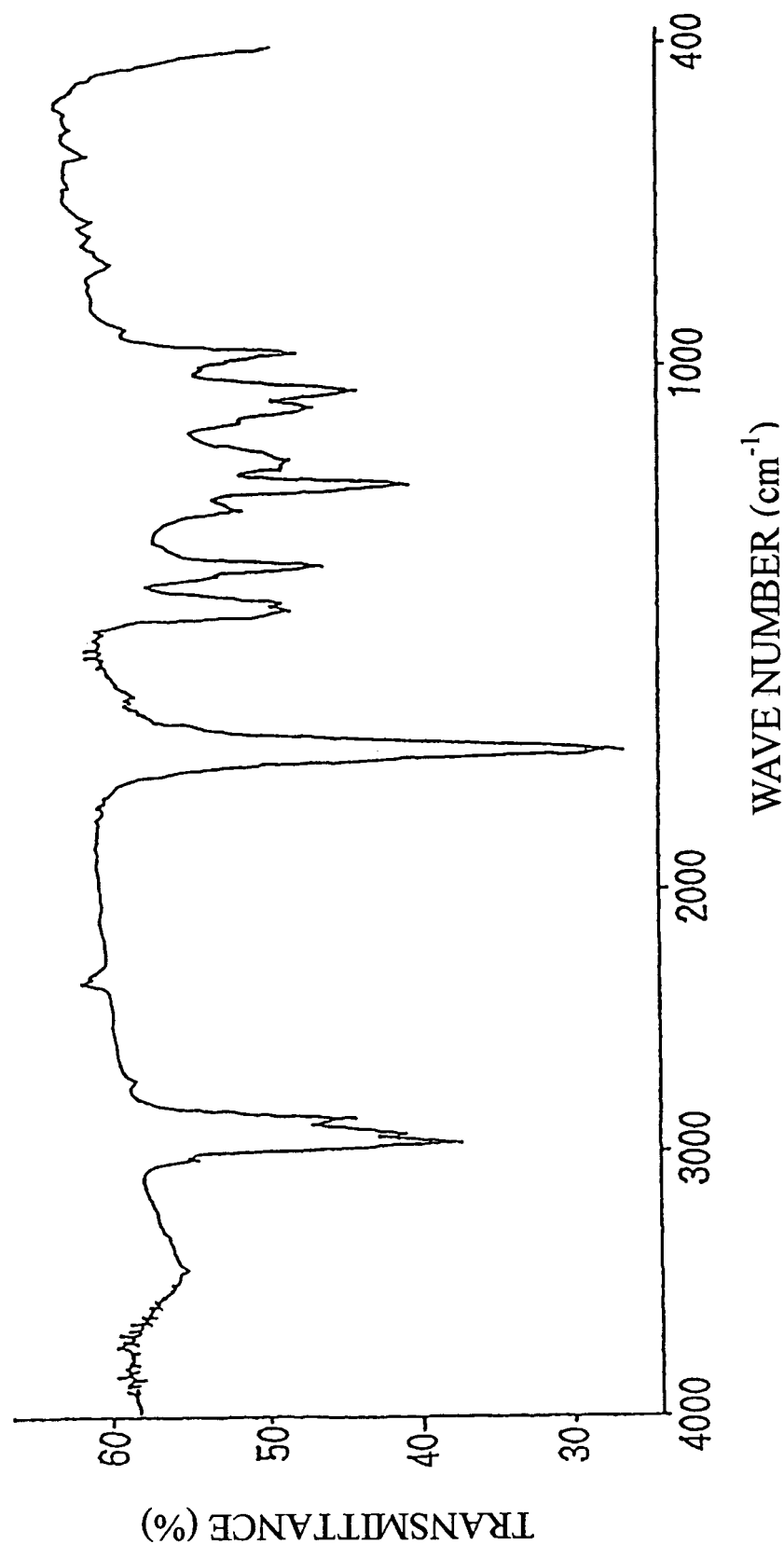
FIG. 7 is a graph showing the results of measurement of an infrared absorption spectrum of α-methyl-β-ethyl-γ-methyl-γ-1-propenyl-δ-valerolactone obtained in Example 4 of the present invention.
Figure 8:
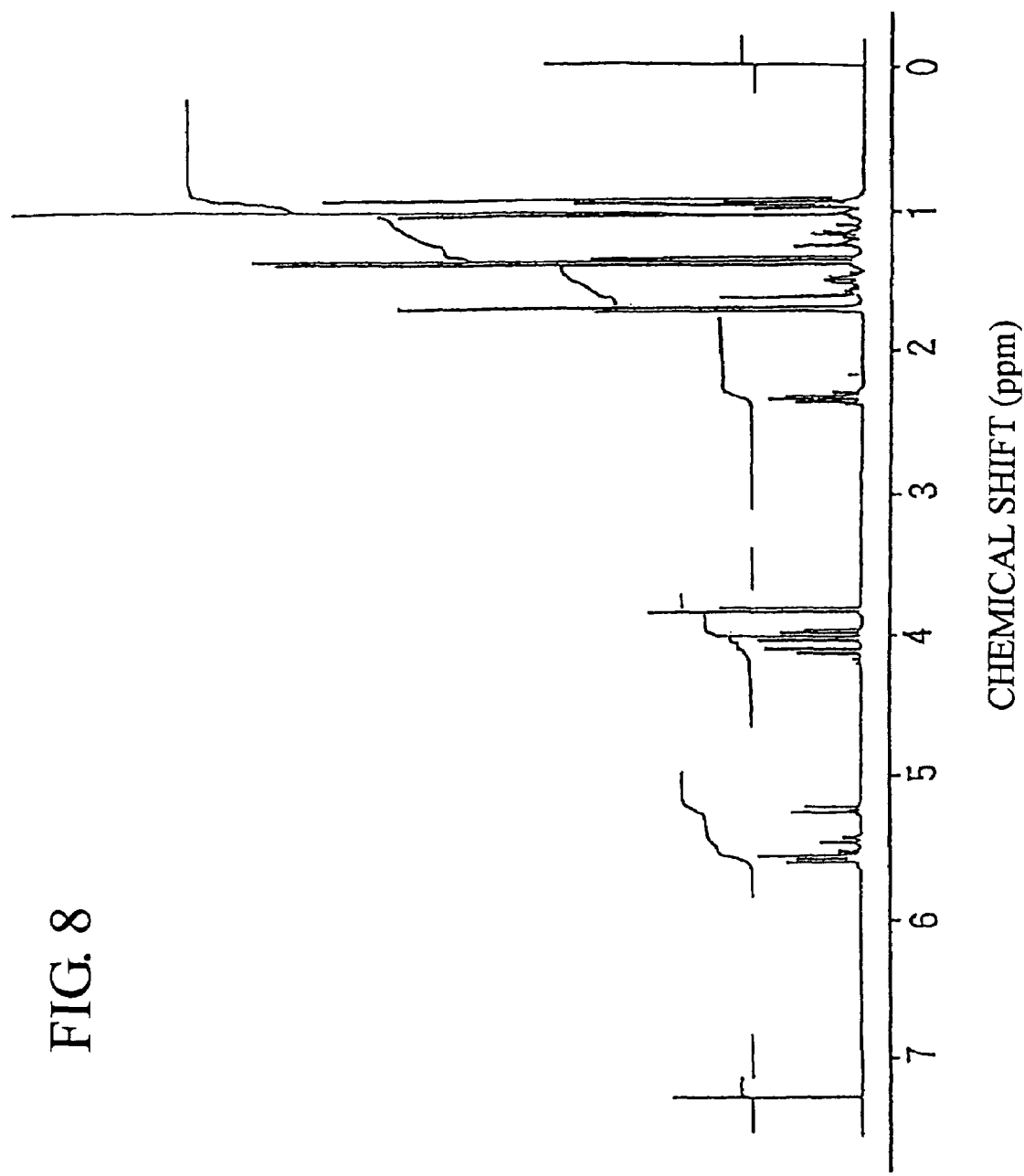
FIG. 8 is a graph showing the results of measurement of $^1$H-NMR (CDCl$_3$) of α-methyl-β-ethyl-γ-methyl-γ-1-propenyl-δ-valerolactone obtained in Example 4 of the present invention.

It was confirmed by an infrared absorption spectrum (IR) and $^1$H-NMR spectrum that the resulting compound was α-methyl-β-ethyl-γ-methyl-γ-1-propenyl-δ-valerolactone (See FIG. 7 and FIG. 8).

Example 5

Synthesis of α-methyl-β-ethyl-γ-methyl-γ-1-propenyl-δ-valerolactone from 2-methyl-2-pentenal A 100 mL four-neck flask equipped with a stirrer and a thermometer was charged with 7.85 g of 2-methyl-2-pentenal and 22 mL of dehydrated methanol, and the mixture was stirred at room temperature for 5 minutes. To the reaction solution was added dropwise 1.23 g of potassium methoxide, and the temperature of the reaction solution was raised to 35° C., followed by the reaction for 6 hours. Thereafter, 20 mL of dehydrated methanol in which 2.24 g of potassium hydroxide had been dissolved was added, and the temperature of the reaction solution was raised to 45° C., followed by stirring for 17 hours.

Next, the resulting reaction solution was cooled to room temperature, and diluted with 100 mL of water and 100 mL of diethyl ether to separate the solution into layers. The ether layer was removed, and the pH of the aqueous layer was adjusted to 2 with hydrochloric acid, followed by extraction with 100 mL of diethyl ether two times. The resulting organic layers were combined, and the solvent was removed under reduced pressure and purified by silica gel column chromatography (hexane:ethyl acetate=4:1 (volume ratio)) to give 1.20 g of α-methyl-β-ethyl-γ-methyl-γ-1-propenyl-δ-valerolactone (yield 15%).

Results of measurement of infrared absorption spectrum (IR) and $^1$H-NMR of the resulting α-methyl-β-ethyl-γ-methyl-γ-1-propenyl-δ-valerolactone are shown in FIG. 7 and FIG. 8, respectively. $^1$H-NMR was measured using 400 MHz NMR manufactured by Varian Inc. Also, infrared absorption spectrum (IR) was measured using Model: FT-IR manufactured by Horiba, Ltd.

In addition, mass spectroscopy of the resulting α-methyl-β-ethyl-γ-methyl-γ-1-propenyl-δ-valerolactone was measured using HP-5973 manufactured by Hewlett-Packard Co. The results are shown below.

[Results of Measurement of Mass Spectroscopy]

(m/z): 196(M+), 166(M$^+$-CH$_2$O)

Example 6

Synthesis of α-methyl-β-ethyl-γ-methyl-γ-propyl-δ-valerolactone

Figure 9:
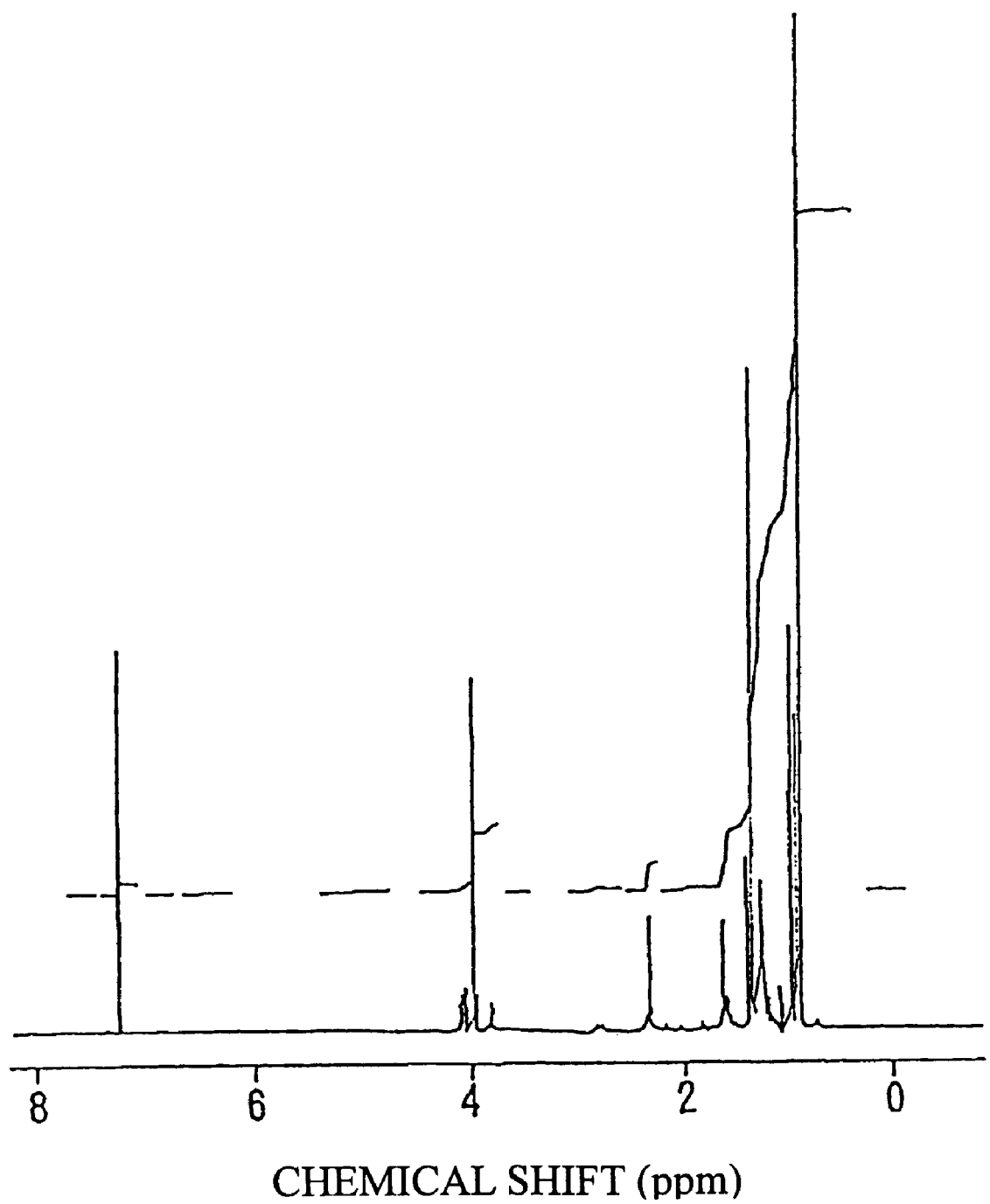
FIG. 9 is an $^1$H-NMR (400 MHz) chart of α-methyl-β-ethyl-γ-methyl-γ-propyl-δ-valerolactone.
Figure 10:
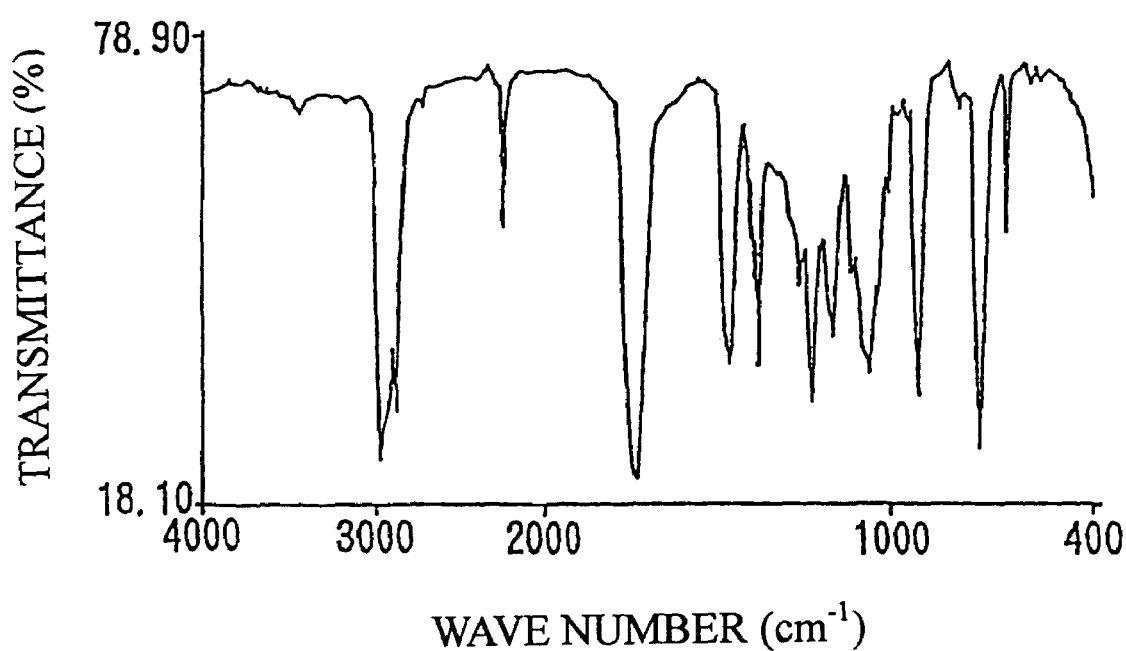
FIG. 10 is a graph showing the results of measurement of an infrared absorption spectrum of α-methyl-β-ethyl-γ-methyl-γ-propyl-δ-valerolactone.

A 100 mL flask for hydrogenation was charged with 0.77 g of α-methyl-β-ethyl-γ-methyl-γ-1-propenyl-δ-valerolactone obtained above, 0.10 g of 5% Pd/C and 10 mL of ethanol, and the mixture was reacted at room temperature for 1 hour under 0.33 MPa (hydrogen pressure: 3.36 kg/cm$^2$). Solid matters were filtered to give 0.70 g of α-methyl-β-ethyl-γ-methyl-γ-propyl-δ-valerolactone. The results of measurement of $^1$H-NMR and infrared absorption spectrum (IR) of the resulting α-methyl-β-ethyl-γ-methyl-γ-propyl-δ-valerolactone are shown in FIG. 9 and FIG. 10, respectively.

Example 7

Preparation of Sandalwood Type Perfume Composition Containing Valerolactone Compound (I)

Using 2-methyl-4-(2,2,3-trimethyl-3-cyclopenten-1-yl)-2-buten-1-ol [trade name: Sandalmysore Core manufactured by Kao Corporation] as a perfume substance having a sandalwood odor, each of perfume compositions $A_1$, $B_1$, $C_1$ and $D_1$ was prepared in a weight ratio of perfumes A, B, C and D as shown in the following Table 1. Using a perfume E as a comparative product, the fragrance of the perfume compositions was evaluated by professional panelists. As a result, as shown below, it was recognized that quality of a sandalwood odor was more enhanced by incorporation of the valerolactone compound represented by formula (II).

TABLE 1

| | Perfume substance Having sandalwood fragrance (% by weight) | Valerolactone compound (II) (% by weight) |
| --- | --- | --- |
| Perfume A | 99.9 | 0.1 |
| Perfume B | 99.8 | 0.2 |
| Perfume C | 99.5 | 0.5 |
| Perfume D | 99.0 | 1.0 |
| Perfume E (Comparison) | 100 | 0 |

<Results of Evaluation>

In the perfume composition $A_1$, a sandalwood note of Sandalmysore core was enhanced as compared with the perfume E as a comparative product. In the perfume composition $B_1$, sweetness and a characteristic of natural sandalwood were recognized as compared with the perfume E as a comparative product. In the perfume composition $C_1$, milk-like sweetness and volume were enhanced as compared with the perfume E as a comparative product, and effect of enhancing a characteristic of natural sandalwood was recognized. In the perfume composition $D_1$, sweetness and a characteristic of natural sandalwood were further enhanced as compared with the perfume E as a comparative product.

Using 2-ethyl-4-(2,2,3-trimethyl-3-cyclopenten-1-yl)-2-buten-1-ol as a perfume substance having a sandalwood odor, the perfume composition $D_2$ was prepared in a weight ratio of the perfume D as described in the above Table 1, and the odor of the perfume composition $D_2$ was evaluated by using the perfume E as a comparative product.

<Results of Evaluation>

In the perfume composition $D_2$, effect of enhancing a woody note was recognized as compared with the perfume E as a comparative product.

Using 3-methyl-5-(2,2,3-trimethyl-3-cyclopenten-1-yl)-pentan-2-ol as a perfume substance having a sandalwood odor, the perfume composition $D_3$ was prepared in a weight ratio of the perfume D described in Table 1, and odor of the perfume composition $D_3$ was evaluated by using the perfume E as a comparative product.

<Results of Evaluation>

To the perfume composition $D_3$, a characteristic of powdery natural sandalwood is imparted, and a soft fragrance was obtained as compared with the perfume E as a comparison product.

Using 3-methyl-5-(2,2,3-trimethyl-3-cyclopenten-1-yl)-4-penten-2-ol as a perfume substance having a sandalwood odor, the perfume composition $D_4$ was prepared in a weight ratio of the perfume D described in Table 1, and the odor of the perfume composition $D_4$ was evaluated by using the perfume E as a comparative product.

<Assessment Result>

In the perfume composition $D_4$, sweetness and volume were recognized as compared with the perfume E as a comparative product.

The perfume substances having a sandalwood odor as shown in Table 1 include, perfumes of which main starting material is camphorenal such as 2-methyl-4-(2,2,3-trimethyl-3-cyclopenten-1-yl)-butanol or 3,3-dimethyl-5-(2,2,3-trimethyl-3-cyclopenten-1-yl)-4-penten-2-ol; isocamphylcyclohexanols; 3,7-dimethyl-7-methoxyoctan-2-ol, in addition to the aforementioned examples.

Example 8

Perfume Composition for Perfume

A composition for perfume showing characteristic soft and sweet woody odor and balsamic odor having a basic natural sandalwood odor could be prepared by adding 1 part by weight of the valerolactone compound represented by the formula (II) to 99 parts by weight of the perfume composition having the components described in the following Table 2.

TABLE 2

| Blended components | Parts by weight |
| --- | --- |
| SANDALMYSORE CORE[*1] | 5 |
| Methyl dihydrojasmonate | 4 |
| γ-Methyl ionone | 3 |
| Bergamot oil | 2 |
| Cyclopentadecanolide | 1 |
| Lemon oil | 1 |
| Benzyl acetate | 0.8 |
| Ylang-ylang oil | 0.6 |
| Citronellol | 0.4 |
| Geraniol | 0.4 |
| Hexyl salicylate | 0.4 |
| Dihydromyrcenol | 0.4 |
| Ethanol | 80 |
| Total | 99 |

[*1]Trade name, manufactured by Kao Corporation, compound name: 2-methyl-4-(2,2,3-trimethyl-3-cyclopenten-1-yl)-2-buten-1-ol

Comparative Example 1

When 1 part by weight of γ-ethyl-γ-butyl-δ-valerolactone was added to 99 parts by weight of the perfume composition obtained in Example 8 (Table 2), the resulting mixture had no sweetness, and had a strong costus-like odor. Therefore, this mixture exhibited an unbalanced odor having no softness like natural sandalwood.

Comparative Example 2

When 1 part by weight of odorless dipropylene glycol was added to 99 parts by weight of the perfume composition obtained in Example 8 (Table 2), the resulting mixture had no sweetness, and had odor remaining of a dry woodiness. Also, softness like natural sandalwood was not recognized.

Example 9

Perfume Composition for Cloth Detergent

When 5 parts by weight of the perfume C obtained in Example 1 was added to 95 parts by weight of the perfume composition having components described in the following Table 3, a perfume composition for a cloth detergent showing cleanness and softness could be obtained.

TABLE 3

| Blended components | Parts by weight |
| --- | --- |
| Orange oil | 20 |
| Methyl dihydrojasmonate | 15 |
| Linalool | 10 |
| Cyclopentadecanolide | 10 |
| p-t-Butyl-α-methylhydrocinnamic aldehyde | 10 |
| α-n-Hexylcinnamic aldehyde | 8 |
| Citronellol | 6 |

TABLE 3-continued

| Blended components | Parts by weight |
| --- | --- |
| Linalyl acetate | 4 |
| γ-Methyl ionone | 3 |
| Acetyl cedrene | 3 |
| o-t-Butylcyclohexyl acetate | 3 |
| Dihydromyrcenol | 2 |
| Methyl β-naphthylketone | 0.8 |
| AMBROXAN[*2] | 0.2 |
| Total | 95 |

[*2]Trade name manufactured by Cognis Co. Ltd., Compound Name: Decahydro-3a,6,6,9a-tetramethylnaphtho[2,1-b]furan

Example 10

Detergent Composition for Cloth

The perfume composition of Example 9 in an amount of 0.4 parts by weight was sprayed to 99.6 parts by weight of a powder detergent composition having components described in the following Table 4, and 20 g of the resulting mixture was weighed. The mixture was dissolved in 30 L of hard water having 3.5° DH. A commercially available cotton towel having a weight of 2 kg was dipped in this aqueous solution, and stirred for 5 minutes, rinsed for 1 minute and dehydrated. When the flavor of this cotton towel was evaluated, a soft and sweet odor was recognized, and the effect of a valerolactone compound represented by the formula (II) was confirmed.

TABLE 4

| Blended components | Parts by weight |
| --- | --- |
| Sodium linear alkyl(C10-C18) benzenesulfonate | 30 |
| Sodium alkyl(C12-C16) sulfate | 5 |
| Polyoxyethylene alkyl ether | 10 |
| Soap (C14-C20) | 5 |
| Crystalline aluminosilicate | 25 |
| Sodium carbonate | 15.6 |
| Sodium sulfate | 6 |
| Polyethylene glycol | 2 |
| Enzyme granules | 1 |
| Total | 99.6 |

Example 11

Perfume Composition for Cloth Softening Agent

When 8 parts by weight of the perfume D obtained in Example 7 (e.g. compositions $D_1, D_2, D_3, D_4$ etc.) was added to 92 parts by weight of a perfume composition having components described in the following Table 5, perfume compositions for a cloth softening agent having a strong and sweet odor giving a volume to the odor could be obtained, respectively.

TABLE 5

| Blended components | Parts by weight |
| --- | --- |
| Muguet type fragrance | 5 |
| Rose type fragrance | 5 |
| Jasmine type fragrance | 3 |
| Orange oil | 10 |
| Tricyclodecenyl acetate | 8 |

TABLE 5-continued

| Blended components | Parts by weight |
|---|---|
| Tricyclodecenyl propionate | 4 |
| γ-Methyl ionone | 8 |
| Acetyl cedrene | 7 |
| Benzyl salicylate | 6 |
| Phenylhexanol | 5 |
| α-n-Hexylcinnamic aldehyde | 5 |
| Methyl dihydrojasmonate | 4 |
| Phenylethyl alcohol | 4 |
| Cyclopentadecanolide | 4 |
| p-t-Butyl-α-methylhydrocinnamic aldehyde | 3 |
| p-t-Butyl cyclohexyl acetate | 3 |
| 4(3)-(4-Hydroxy-4-methylpentyl)-3-cyclohexene-1-carboxyaldehyde | 2 |
| Methyl β-naphthyl ketone | 2 |
| Anise aldehyde | 2 |
| Patchouli oil | 1.5 |
| AMBROXAN*2 | 0.5 |
| Total | 92 |

*2Trade name manufactured by Cognis Co. Ltd., Compound Name: Decahydro-3a,6,6,9a-tetramethylnaphtho[2,1-b]furan Example 12

Softening Composition for Cloth

The perfume composition of Example 11 in an amount of 5 parts by weight was added to 99.5 parts by weight of a softening agent composition having components described in the following Table 6, and 3 g of the mixture was weighed. The mixture was dissolved in 30 L of water. A commercially available cotton towel having a weight of 2 kg was dipped in this aqueous solution, and stirred at 25° C. for 1 minute. After dehydration, the cotton towel was dried at room temperature; the odor of the cotton towel was evaluated on the next day. As a result, a natural sandalwood-like odor was felt together with musk-like, amber-like and floral-like odor even in a dried cloth, and sweet odor was continued.

TABLE 6

| Blended components | Parts by weight |
|---|---|
| Distearyldimethylammonium chloride (manufactured by Kao Corporation under the trade name of QUARTAMIN D86P) | 15 |
| Silicone compound | 0.01 |
| Calcium chloride | 0.05 |
| Ethanol | 2 |
| Water | 82.44 |
| Total | 99.5 |

Example 13

Perfume Composition for Shampoo

When 5 parts by weight of the perfume D obtained in Example 7 (e.g. compositions $D_1$, $D_2$, $D_3$, $D_4$ etc.) was added to 95 parts by weight of a perfume composition having components described in the following Table 7, perfume compositions for a shampoo having a soft and sweet odor intrinsic in natural sandalwood could be obtained, respectively.

TABLE 7

| Blended components | Parts by weight |
|---|---|
| Linalool | 15 |
| Cyclopentadecanolide | 12 |
| Methyl dihydrojasmonate | 12 |
| p-t-Butyl-α-methylhydrocinnamic aldehyde | 10 |
| Cis-3-hexenyl salicylate | 10 |
| Dimethylbenzyl carbinyl acetate | 5 |
| Citronellol | 5 |
| Phenylethyl alcohol | 5 |
| AMBER CORE*3 | 5 |
| α-n-Hexylcinnamic aldehyde | 4 |
| Benzyl acetate | 4 |
| Orange oil | 3 |
| Linalyl acetate | 3 |
| γ-Methyl ionone | 2 |
| Total | 95 |

*3Trade name manufactured by Kao Corporation, Compound Name: 1-(2-t-Butylcyclohexyloxy)-2-butanol Example 14

Perfume Composition for Liquid Body Shampoo

When 10 parts by weight of the perfume D obtained in Example 7 (e.g. compositions $D_1$, $D_2$, $D_3$, $D_4$ etc.) was added to 90 parts by weight of a perfume composition having components described in the following Table 8, perfume compositions for a liquid body shampoo characterized in remaining of a soft and sweet odor on a skin could be obtained, respectively.

TABLE 8

| Blended components | Parts by weight |
|---|---|
| Muguet type fragrance | 15 |
| Rose type fragrance | 10 |
| Linalool | 8 |
| AMBER CORE*3 | 8 |
| Methyl dihydrojasmonate | 8 |
| Orange oil | 5 |
| β-Ionone | 5 |
| n-Hexyl salicylate | 5 |
| o-t-Butyl cyclohexyl acetate | 5 |
| Cyclopentadecanolide | 5 |
| Patchouli oil | 4 |
| 4(3)-(4-Hydroxy-4-methylpentyl)-3-cyclohexene-1-carboxyaldehyde | 4 |
| Dimethylbenzyl carbinyl n-butyrate | 4 |
| γ-Undecalactone | 2 |
| Piperonal | 2 |
| Total | 90 |

*3Trade name manufactured by Kao Corporation, Compound Name: 1-(2-t-Butylcyclohexyloxy)-2-butanol Example 15

Perfume Composition for Incense Stick

When 5 parts by weight of the valerolactone compound represented by the formula (II) was added to 95 parts by weight of a perfume composition having components described in the following Table 9, a perfume composition for an incense stick having an oriental sweet odor like perfume could be obtained.

TABLE 9

| Blended components | Parts by weight |
|---|---|
| Bergamot oil | 10 |
| Patchouli oil | 10 |
| Vetiver oil | 3 |
| Cinnamon oil | 1 |
| Nutmeg oil | 1 |
| Clove bud oil | 1 |
| Dihydromyrcenol | 10 |
| Linalool | 3 |
| SANDALMYSORE CORE*1 | 10 |
| Isocamphyl cyclohexanol | 10 |
| AMBER CORE*3 | 10 |
| Acetyl cedrene | 10 |
| Cyclopentadecanolide | 10 |
| Vanillin | 4 |
| Piperonal | 1 |
| *Cistus landanifer* absolute | 1 |
| Total | 95 |

*1Trade name manufactured by Kao Corporation, Compound name: 2-methyl-4-(2,2,3-trimethyl-3-cyclopenten-1-yl)-2-buten-1-ol
*3Trade name manufactured by Kao Corporation, Compound name: 1-(2-t-butylcyclohexyloxy)-2-butanol

Example 16

Flavor Composition for Imparting Milk Flavor

When 0.8 part by weight of the valerolactone compound represented by the formula (II) was added to 99.2 parts by weight of a flavor composition having components described in the following Table 10, a perfume composition for imparting a milk flavor, having volume and a natural milk flavor could be obtained.

TABLE 10

| Blended components | Parts by weight |
|---|---|
| Dimethyl sulfide | 0.01 |
| Cis-3-hexenol | 0.05 |
| 2-Nonanone | 0.02 |
| 2-Undecanone | 0.03 |
| Acetoin | 0.01 |
| Diacetyl | 0.01 |
| Butyl dibutyryl lactate | 0.10 |
| Ethyl levulinate | 0.05 |
| Ethyl myristate | 0.20 |
| Ethylhexanoate | 0.20 |
| δ-Undecalactone | 1.00 |
| δ-Dodecalactone | 1.20 |
| Butyric acid | 0.30 |
| Octanoic acid | 0.30 |
| Decanoic acid | 1.00 |
| Lauric acid | 1.00 |
| Myristic acid | 0.10 |
| Ethyl maltol | 0.10 |
| Vanillin | 0.10 |
| Propylene glycol | 93.42 |
| Total | 99.20 |

Example 17

Milk Coffee Composition

When 0.1 part by weight of the flavor composition of Example 16 was added to 99.9 parts by weight of a milk coffee composition having components described in the following Table 11, a milk coffee composition having rich sweetness and a suitable bitter flavor could be obtained.

TABLE 11

| Blended components | Parts by weight |
|---|---|
| Regular coffee | 6.00 |
| Coffee extract | 2.00 |
| Skim milk powder | 0.60 |
| Whole milk powder | 0.70 |
| Granulated sugar | 8.00 |
| Sugar ester | 0.06 |
| Sodium hydrogen carbonate | 0.08 |
| Coffee flavor | 0.10 |
| Water | 82.36 |
| Total | 99.90 |

Example 18

Perfume Composition

When 50 parts by weight of the valerolactone compound (II), 10 parts by weight of the valerolactone compound (III), 30 parts by weight of the valerolactone compound (IV) and 10 parts by weight of the valerolactone compound (VII) were mixed together, a woody and sandal-like perfume composition reminding of floral and costus was obtained.

Example 19

Perfume Composition

When 40 parts by weight of the valerolactone compound (II) was combined with 60 parts by weight of the valerolactone compound (V), a coumarin type perfume composition reminding of a woody odor and a coumarin-like sweetness odor was obtained.

INDUSTRIAL APPLICABILITY

The valerolactone compound can be arbitrarily combined with various perfumes. The perfume composition containing the valerolactone compound can be used in or applied to various aromatic products, for example, in the field of household products, personal and cosmetic products, and environmental hygiene products.

What is claimed is:

1. A valerolactone compound represented by the formula (II):

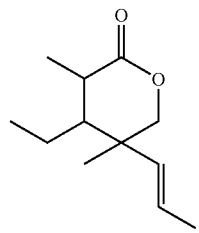

2. The valerolactone compound according to claim 1, obtained by acting a base on propanal, and treating the resulting reaction solution with an acid.

3. The valerolactone compound according to claim 2, wherein said base is one or more compounds selected from the group consisting of potassium hydroxide, sodium hydroxide, potassium methoxide and sodium methoxide.

4. A perfume composition comprising the valerolactone compound as defined in claim 2.

5. A process for preparing a valerolactone represented by the formula (II):

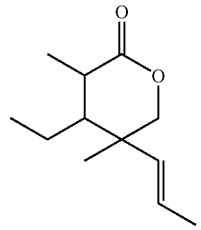
(II)

comprising acting a base on propanal, and treating the resulting reaction solution with an acid.

6. A process for preparing a valerolactone represented by the formula (II):

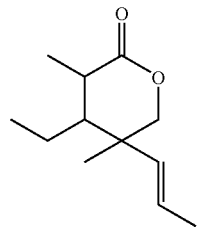
(II)

comprising acting a base on 2-methyl-2-pentenal, and treating the resulting reaction solution with an acid.

7. The process for preparing a valerolactone compound according to claim 5 or 6, wherein said base is one or more compounds selected from the group consisting of potassium hydroxide, sodium hydroxide, potassium methoxide and sodium methoxide.

8. The process of claim 5, which comprises:
(a) reacting propanal with a base, to obtain a compound of formula (L):

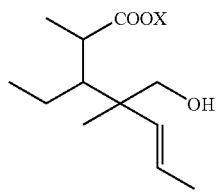
(L)

wherein X is K, Na, Ca, or Mg; and
(b) treating said compound of formula (L) with an acid to obtain said valerolactone compound.

9. The process of claim 6, which is obtained by a process comprising:
(a) reacting 2-methyl-2-pentenal with a base, to obtain a compound of formula (L):

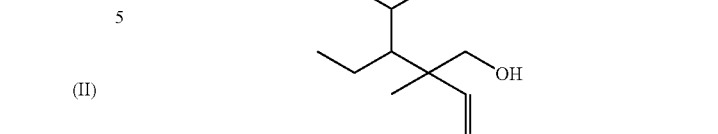
(L)

wherein X is K, Na, Ca, or Mg; and
(b) treating said compound of formula (L) with an acid to obtain said valerolactone compound.

10. A perfume composition comprising a valerolactone compound represented by the formula (II):

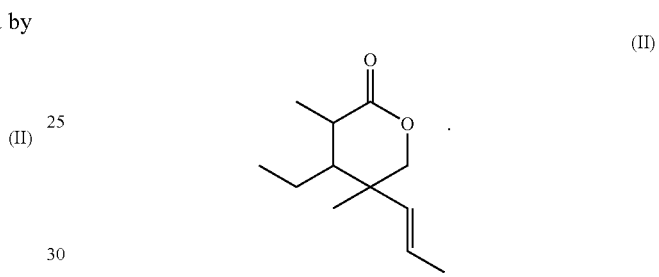
(II)

11. A perfume composition comprising a compound selected from the group consisting of:

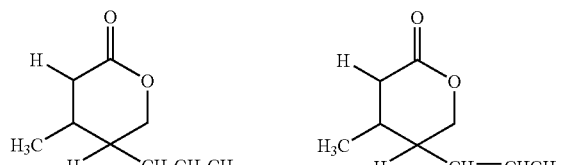

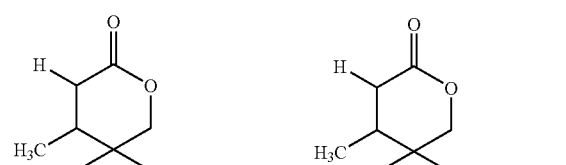

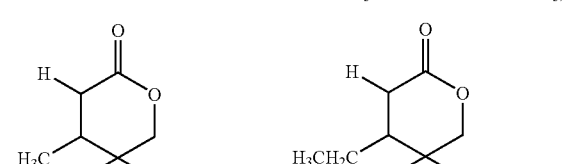

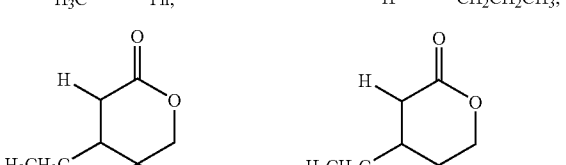

-continued
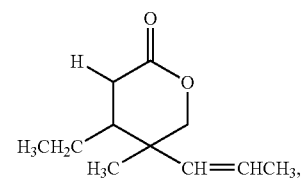
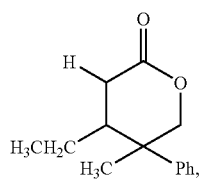
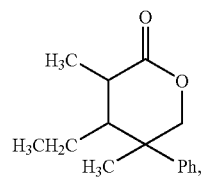
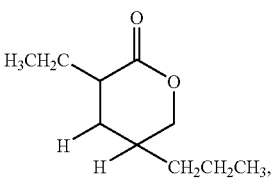
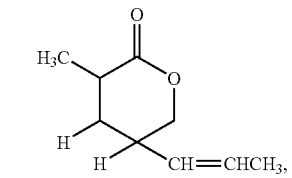
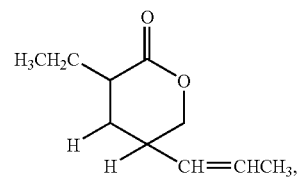
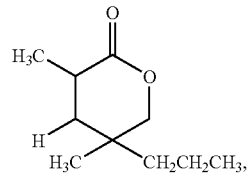
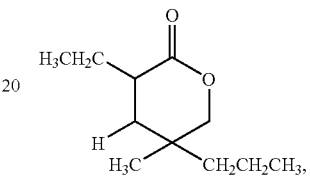
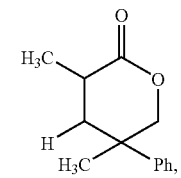
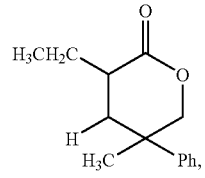
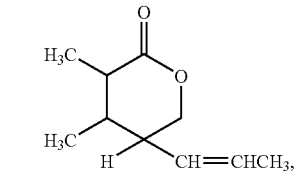
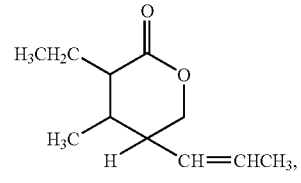
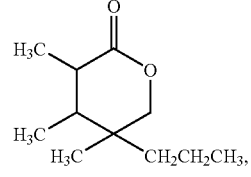
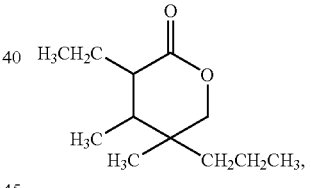
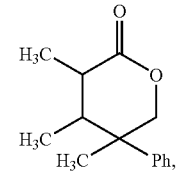
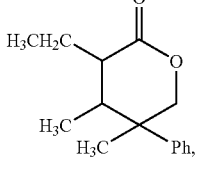
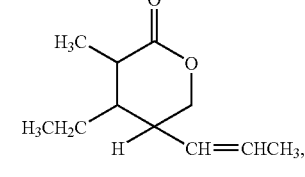
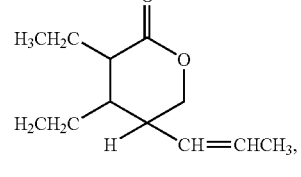
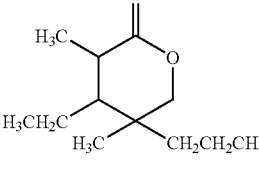
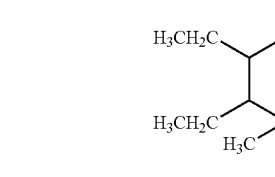

-continued

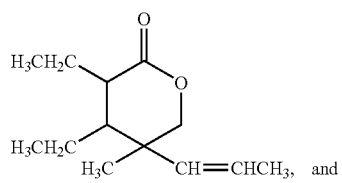 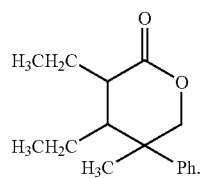

12. The perfume composition according to claim 10 or 11, further comprising one or more compounds selected from the group consisting of the following compounds represented by the formulae (III) to (VII):

(III)

(IV)

(V)

(VI)

(VII)

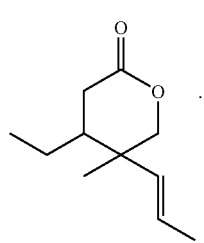

13. The perfume composition according to claim 10 or 11, wherein the content of said valerolactone compound is at least 0.001% by weight.

14. The perfume composition according to claim 10, wherein the content of said valerolactone compound is at least 0.2% by weight.

15. A perfume composition comprising two or more compounds selected from the group consisting of the following compounds represented by the formulae (III) to (VII):

(III)

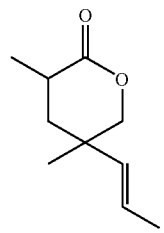

(IV)

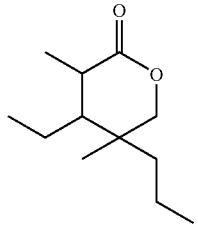

(V)

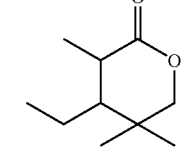

(VI)

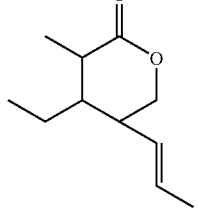

(VII)

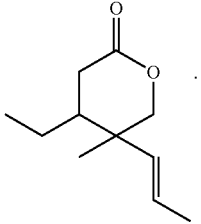

16. The perfume composition according to claim 10 or 11, further comprising a perfume of which main starting material is a camphorenal.

17. The perfume composition according to claim 10 or 11, further comprising one or more compounds selected from the group consisting of the following components (A):

(A) 2-ethyl-4-(2,2,3-trimethyl-3-cyclopenten-1-yl)-2-buten-1-ol, 3-methyl-5-(2,2,3-trimethyl-3-cyclopenten-1-yl)-pentan-2-ol, 2-methyl-4-(2,2,3-trimethyl-3-cyclopenten-1-yl)-butanol, 3,3-dimethyl-5-(2,2,3-trimethyl-3-cyclopenten-1-yl)-4-penten-2-ol, 3-methyl-5-(2,2,3-trimethyl-3-cyclopenten-1-yl)-4- penten-2-ol, 2-methyl-4-(2,2,3-trimethyl-3-cyclopenten-1-yl)-2-buten-1-ol, and optical isomers thereof.

18. The perfume composition according to claim 17, wherein the weight ratio of the compound represented by the formula (I) to the component (A) is at least 1:100,000.

19. The perfume composition according to claim 17, wherein the weight ratio of the compound represented by the formula (I) to the component (A) is at least 1:500.

20. A compound selected from the group consisting of:

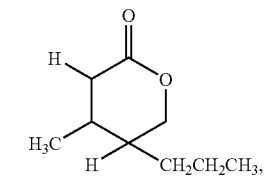
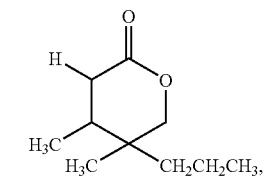
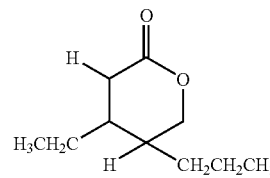
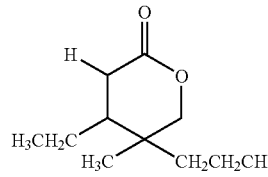
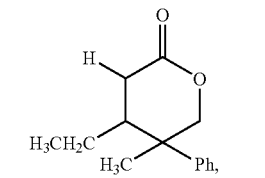
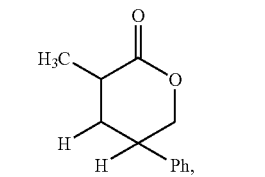
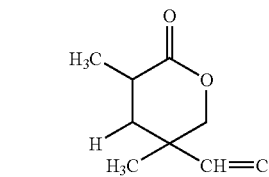
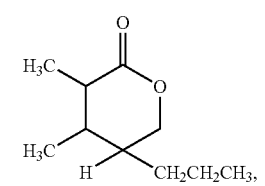
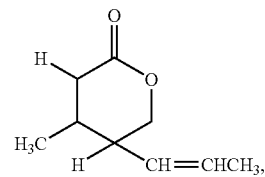
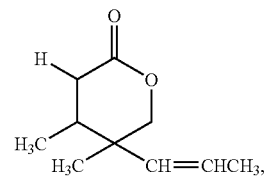
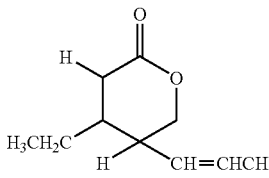
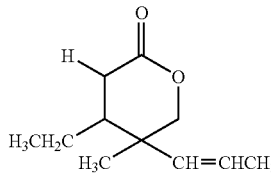
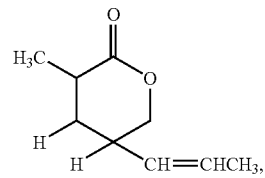
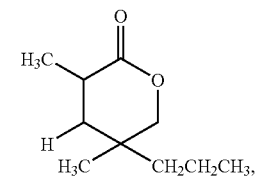
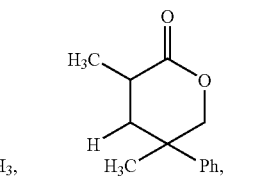
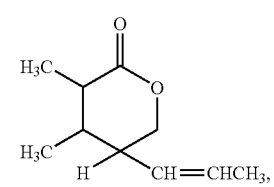

-continued

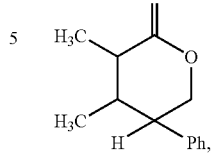
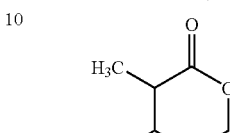
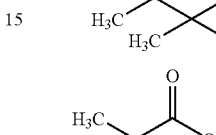
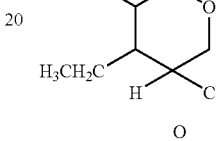
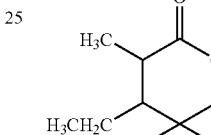
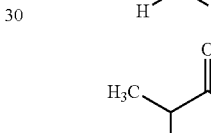
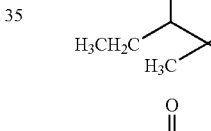
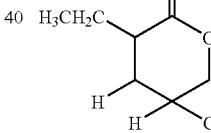
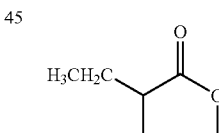
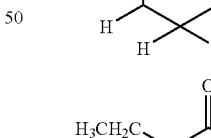
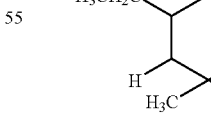
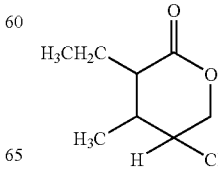
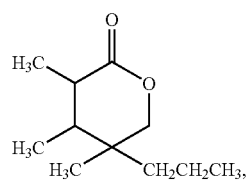
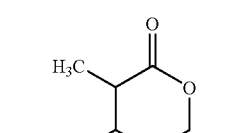
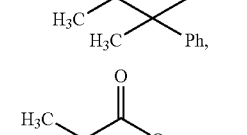
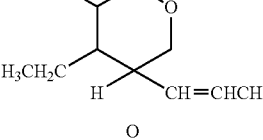
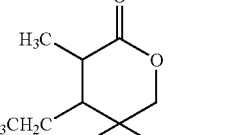
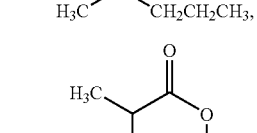
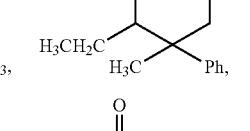
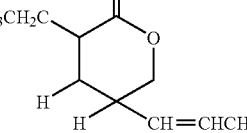
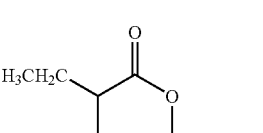
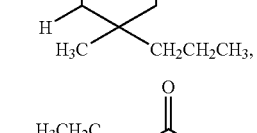
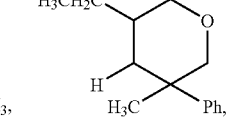
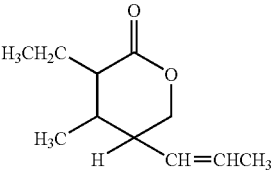

-continued
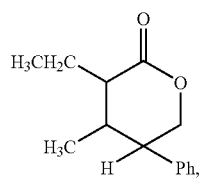 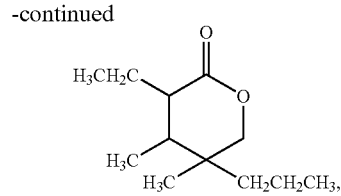
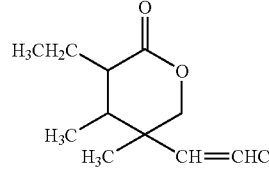 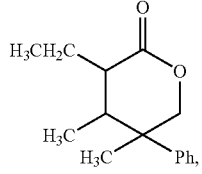
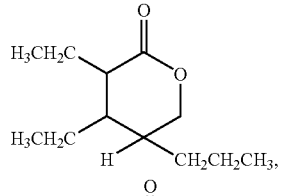 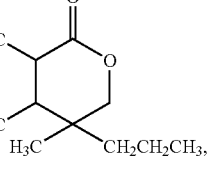
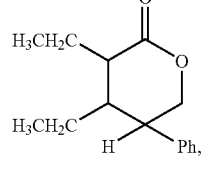 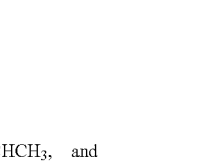
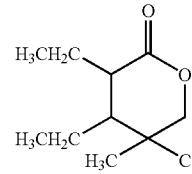, and
-continued
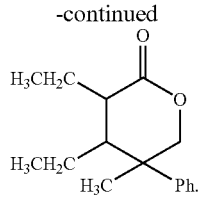
21. The valerolactone compound of claim 2, which is obtained by a process comprising:
   (a) reacting propanal with a base, to obtain a compound of formula (L):
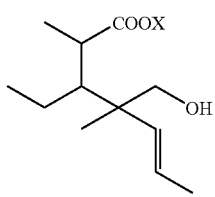
(L)
wherein X is K, Na, Ca, or Mg; and
   (b) treating said compound of formula (L) with an acid to obtain said valerolactone compound.
* * * * *